(12) United States Patent
Hirayama et al.

(10) Patent No.: US 6,642,224 B1
(45) Date of Patent: Nov. 4, 2003

(54) DIAZEPAN DERIVATIVES OR SALTS THEREOF

(75) Inventors: Fukushi Hirayama, Tsukuba (JP); Hiroyuki Koshio, Tsukuba (JP); Tsukasa Ishihara, Tsukuba (JP); Norio Seki, Tsukuba (JP); Shunichiro Hachiya, Tsukuba (JP); Keizo Sugasawa, Tsukuba (JP); Ryota Shiraki, Tsukuba (JP); Yuji Koga, Tsukuba (JP); Yuzo Matsumoto, Tsukuba (JP); Takeshi Shigenaga, Tsukuba (JP); Souichirou Kawazoe, Tsukuba (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/148,544

(22) PCT Filed: Mar. 29, 2001

(86) PCT No.: PCT/JP01/02673
§ 371 (c)(1),
(2), (4) Date: Oct. 2, 2002

(87) PCT Pub. No.: WO01/74791
PCT Pub. Date: Oct. 11, 2001

(30) Foreign Application Priority Data

Mar. 31, 2000 (JP) ........................ 2000-096858

(51) Int. Cl.[7] ............... A61K 31/55; A61P 7/02; C07D 223/04; C07D 401/00
(52) U.S. Cl. .................. 514/217.04; 514/217.12; 540/597; 540/610
(58) Field of Search ................ 540/597, 610; 514/217.04, 217.12

(56) References Cited

U.S. PATENT DOCUMENTS

| | | | |
|---|---|---|---|
| 5,869,501 A | 2/1999 | Hirayama et al. | 514/319 |
| 6,140,351 A | 10/2000 | Arnaiz et al. | 514/336 |
| 6,313,122 B1 | 11/2001 | Beight et al. | 514/237.5 |
| 6,313,151 B1 | 11/2001 | Beight et al. | 514/352 |
| 6,372,759 B1 | 4/2002 | Beight et al. | 514/318 |
| 6,376,515 B2 | 4/2002 | Zhu et al. | 514/318 |
| 6,380,221 B1 | 4/2002 | Arnaiz et al. | 514/337 |
| 6,417,200 B1 | 7/2002 | Beight et al. | 514/330 |
| 2002/0002183 A1 | 1/2002 | Zhu et al. | 514/318 |
| 2002/0091116 A1 | 7/2002 | Zhu et al. | 514/211.15 |

FOREIGN PATENT DOCUMENTS

| | | |
|---|---|---|
| EP | 0 798 295 | 10/1997 |
| JP | 2000-302765 | 10/2000 |
| WO | WO96/169410 | 6/1996 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/32477 | 7/1999 |
| WO | WO99/37643 | 7/1999 |
| WO | WO 00/39111 | 7/2000 |
| WO | WO 00/39117 | 7/2000 |
| WO | WO 00/39118 | 7/2000 |
| WO | WO 01/19788 | 3/2001 |
| WO | WO 01/19798 | 3/2001 |
| WO | WO 01/64642 | 9/2001 |
| WO | WO 01/64643 | 9/2001 |

*Primary Examiner*—Brenda Coleman
(74) *Attorney, Agent, or Firm*—Fitzpatrick, Cella, Harper & Scinto

(57) ABSTRACT

To provide a compound which has an anticoagulation action based upon inhibition of activated blood coagulation factor X and is useful as an anticoagulant or an agent for prevention and treatment of diseases caused by thrombus or embolus. A diazepan derivative such as 4-[(3-carbamimidoylphenylamino)methyl]-3-[4-(4-methyl-1,4-diazepan-1-yl)benzoylamino]benzoic acid and 3-hydroxy-4'-methoxy-2-{[4-(4-methyl-1,4-diazepan-1-yl)benzoyl]amino}benzanilide or a salt thereof is an effective ingredient.

6 Claims, No Drawings

DIAZEPAN DERIVATIVES OR SALTS THEREOF

CROSS-REFERENCE TO RELATED APPLICATIONS

This application is a national stage entry under 35 U.S.C. §371 of PCT/JP01/02673 filed Mar. 29, 2001.

TECHNICAL FIELD

This invention relates to a novel diazepan derivative or a salt thereof, which is useful as a pharmaceutical particularly as an activated blood coagulation factor X inhibitor and also to such a pharmaceutical agent.

BACKGROUND ART

With the changes into European and American life styles and the increase in aged population in recent years, the number of patients with thromboembolic diseases including myocardial infarction, cerebral thrombosis and peripheral arterial thrombosis have been increasing year by year and social importance of their treatment has been increasing more and more. As well as the fibrinolysis therapy and antiplatelet therapy, the anticoagulation therapy takes a part of the medical therapy in treating and preventing thrombosis (*Sogo Rinsho*, 41: 2141–2145, 1989). In particular, the safety which withstands long-term administration and accurate and proper expression of the anticoagulation activity are essential in the prevention of thrombosis. Warfarin potassium is frequently used in the world as the sole oral anticoagulant but this drug is extremely difficult to use clinically because it is difficult to control the anticoagulation capacity due to the characteristics based on its action mechanism (*J. Clinical Pharmacology*, 32, 196–209, 1992 and *N. Eng. J. Med.*, 324(26), 1865–1875, 1991) whereby a great concern has been directed toward the development of more useful and easily usable anticoagulants.

Thrombin controls conversion of fibrinogen into fibrin which is the final step of coagulation and is also concerned deeply in the activation and aggregation of platelets ("T-PA and Pro-UK" edited by S. Matsuo, published by Gakusai Kikaku, pp. 5–40 "Blood Coagulation", 1986) and its inhibitor has been the center of anticoagulant studies as a target of development of pharmaceuticals. However, thrombin inhibitors which can be administered orally have not been put into the market until now because of their low bioavailability by oral administration and problems from the viewpoint of safety (*Biomed. Biochim. Acta*, 44, 1201–1210, 1985).

Activated blood coagulation factor X is a key enzyme which is located at the joining point of the extrinsic and intrinsic coagulation cascade reactions and located upstream to thrombin whereby there is a possibility that inhibition of this factor is more efficient than the thrombin inhibition and such an inhibitor can inhibit this coagulation system in a specific manner (*THROMBOSIS RESEARCH* (19), 339–349, 1980).

As the compounds having an activated blood coagulation factor X inhibiting action, amidinonaphthyl alkylbenzene derivatives or salts thereof have been known (Japanese Patent Laid-Open No. 208946/1993; *Thrombosis Haemostasis*, 71(3), 314–319, 1994; and *Thrombosis Haemostasis*, 72(3), 393–396, 1994).

In WO 96/16940, it is mentioned that an amidinonaphthyl derivative or a salt thereof represented by the following general formula is the compound having an activated blood coagulation factor X inhibiting action (Prior Art 1).

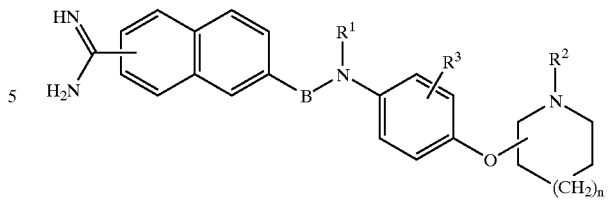

(For the symbols in the formula, refer to the gazette.)

In WO99/00121, WO99/00126, WO99/00127, WO99/00128, WO00/39111, WO00/39117 and WO00/39118, phenylenediamide compounds, etc. represented by the following general formula are mentioned as an factor Xa inhibitor (Prior Art 2).

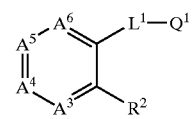

(For the symbols in the formula, refer to the gazette.)

Further, in WO99/32477, a broad range of compounds represented by the following general formula is mentioned as an anticoagulant (Prior Art 3).

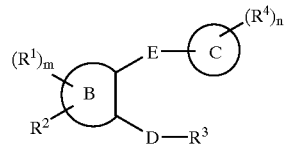

(For the symbols in the formula, refer to the gazette.)

DISCLOSURE OF THE INVENTION

The present inventors have produced a diazepan derivative represented by the following general formula (I) or a salt thereof and found that it has an excellent activated blood coagulation factor X inhibiting action and particularly has an excellent activity by oral administration.

Specifically, this invention relates to a diazepan derivative represented by the following general formula (I) or a salt thereof and also to a pharmaceutical composition, particularly an activated blood coagulation factor X inhibitor, containing the same as an effective ingredient.

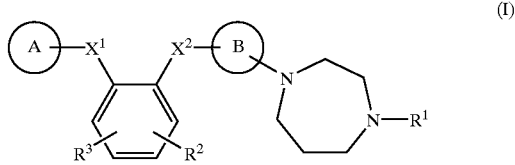

(Symbols in the above formula have the following meanings:

Rings A and B: They are the same or different and are each aryl or heteroaryl which may have 1 to 3 substituents;

$X^1$: —C(=O)—$NR^4$—, —$NR^4$—C(=O)—, —$NR^4$—$CH_2$—, —O—$CH_2$—, —$CH_2$—$CH_2$— or —CH=CH—;

$X^2$: —C(=O)—$NR^5$— or —$NR^5$—C(=O)—;

$R^1$: hydrogen atom, lower alkyl, -lower alkylene-O-lower alkyl, $C_{3-8}$ cycloalkyl, aryl, heteroaryl, -lower alkylene- $C_{3-8}$ cycloalkyl, -lower alkylene-aryl, -lower alkylene-heteroaryl or —C(=NR$^6$)-lower alkyl;

$R^2$: —OH, —O-lower alkyl, —O-lower alkylene-OH, —O—SO$_2$—OH, —O-lower alkylene-COOH, —O-lower alkylene-COO-lower alkyl, —COOH, —COO-lower alkyl or halogen atom;

$R^3$: hydrogen atom, halogen atom or lower alkyl; and $R^4$, $R^5$ and $R^6$: They are the same or different and are each hydrogen atom or lower alkyl.)

The compound of this invention (I) has a different structure from the compounds mentioned in the Prior Art 1 in such a respect that it has a diazepan-1-yl group and at least four cyclic moieties and that the nitrogen atom of diazepan is directly linked to a ring B. Further, the compound of this invention has a different structure from the Prior Art 2 in such a respect that it has a diazepan-1-yl group. Moreover, in the Prior Art 3, no compound having a diazepan-1-yl group is specifically mentioned. Thus, the characteristic feature of the compound (I) of this invention in terms of chemical structure is that diazepanylaryl or diazepanylheteroaryl is linked to a benzene ring via an amide linkage, that the benzene ring is further linked to aryl or heteroaryl via an amide linkage and further that the benzene ring has —OH, —O-lower alkyl or halogen atom, etc.

As hereunder, the compound (I) of this invention will be illustrated in detail.

The term "lower" in the definition for the general formula in the specification means a straight or branched carbon chain having 1 to 6 carbons unless otherwise mentioned. Therefore, examples of the "lower alkyl" for $R^1$ to $R^6$ and of that exemplified for the substituents which will be mentioned later are methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-timethylpropyl, 1,2,2-trimethylpropyl, 1-ethyl-1-methylpropyl and 1-ethyl-2-methylpropyl. Among them, those having 1 to 3 carbons are preferred and methyl and ethyl are particularly preferred.

"Lower alkylene" means $C_{1-6}$ alkylene that is one in which arbitrary one hydrogen atom has been removed from the above-described "lower alkyl" and is preferably methylene, ethylene, propylene or isopropylene.

"Aryl" means an aromatic hydrocarbon ring including a fused ring and is preferably aryl having 6 to 14 carbons, and more preferably phenyl, naphthyl, etc.

"Heteroaryl" means a heterocyclic aryl having 1 to 4 same or different heteroatoms selected from a group consisting of N, S and O including a fused ring and its specific examples are furyl, thienyl, pyrrolyl, imidazolyl, pyrazolyl, isothiazolyl, isoxazolyl, triazolyl, tetrazolyl, pyridyl, pyrimidinyl, pyridazinyl, pyrazinyl, indolyl, indazolyl, indolidinyl, quinolyl, isoquinolyl, quinazolinyl, quinolidinyl, quinoxalinyl, cinnolinyl, benzimidazolyl, imidazopyridyl, benzofuranyl, dihydrobenzofuranyl, naphthylidinyl, 1,2-benzoisoxazolyl, benzoxazolyl, benzothiazolyl, oxazolopyridyl, isothiazolopyridyl and benzothienyl although this invention is not limited thereto.

"$C_{3-8}$ cycloalkyl" means a cycloalkyl having 3 to 8 carbons and is particularly preferably cyclopropyl or cyclobutyl.

Examples of the "substituent" for "aryl or heteroaryl which may have 1 to 3 substituents" are optionally substituted lower alkyl, lower alkenyl, lower alkynyl, $C_{3-8}$ cycloalkyl, optionally —O-substituted lower alkyl, halogen atom, —NH$_2$, —NH-lower alkyl, —N-(lower alkyl)$_2$, —C(=NH)—NH$_2$, —C(=N—OH)—NH$_2$, —C(=NH)—NH—OH, —C(=NH)—NH—C(=O)—O-lower alkyl, —COOH, optionally —C(=O)—O-substituted lower alkyl, optionally —C(=O)—O-substituted $C_{6-14}$ aryl, optionally —C(=O)—O-substituted heteroaryl, —CN, —NO$_2$, —OH, optionally —O—CO-substituted lower alkyl, —O—CO—NH$_2$, —O—CO—NH-lower alkyl, —O—CO—N-(lower alkyl)$_2$, —SH, —C(=32 O)—NH$_2$, —C(=O)—NH-(lower alkyl) and —C(=O)—N-(lower alkyl)$_2$.

Examples of the substituent for the "optionally substituted lower alkyl, lower alkenyl, lower alkynyl or $C_{3-8}$ cycloalkyl", "optionally substituted $C_{6-14}$ aryl" or "optionally substituted heteroaryl" are halogen atom, —COOH, —C(=O)—O-lower alkyl, —OH, —NH$_2$, —NH-lower alkyl and —N-(lower alkyl)$_2$.

Examples of the "halogen atom" are fluorine atom, chlorine atom, iodine atom and bromine atom. Particularly, chlorine atom and bromine atom are preferred.

Incidentally, $R^1$ is preferably lower alkyl, and particularly preferably methyl. $R^2$ is particularly preferably —OH. $R^4$ to $R^6$ are the same or different and are each hydrogen atom or lower alkyl, and more preferably hydrogen atom. Further, $X^1$ is preferably —C(=O)—NR$^4$—, —NR$^4$—C(=O)—, —NR$^4$—CH$_2$— or —O—CH$_2$—, and particularly preferably —C(=O)—NR$^4$— or —NR$^4$—C(=O)—. $X^2$ is —C(=O)—NR$^5$— or —NR$^5$—C(=O)—, and more preferably —NR$^5$—C(=O)—.

Ring A and ring B are the same or different and are desirably benzene ring, pyridine ring, naphthalene ring, thiophene ring, benzofuran ring or quinoline ring, and particularly preferably benzene ring.

Of the compounds of this invention, particularly preferred specific examples include 3-hydroxy-4'-methoxy-2-{[4-(4-methyl-1,4-diazepan-1-yl)benzoyl]amino}benzanilide, 3-hydroxy-N$^1$-(4-methoxybenzoyl)-N$^2$-[4-(4-methyl-1,4-diazepan-1-yl)benzoyl]-1,2-phenylenediamine, 5-chloro-N-(5-chloro-2-pyridyl)-3-hydroxy-2-{[4-(4-methyl-1,4-diazepan-1-yl)benzoyl]amino}benzamide, 5-chloro-3-hydroxy-4'-methoxy-2-{[4-(4-methyl-1,4-diazepan-1-yl)benzoyl-amino}benzanilide and 5-bromo-N-(5-chloro-2-pyridyl)-3-hydroxy-2-{[4-(4-methyl-1,4-diazepan-1-yl)benzoyl]amino}-benzamide or salts thereof.

The compound of this invention includes various isomers such as geometrical isomers, tautomers and optical isomers, either as mixtures or in isolated forms.

The compound (I) of this invention may form an acid addition salt. Further, it may form a salt with a base depending upon the type of the substituent. Specific examples of such a salt are acid addition salts with a mineral acid such as hydrochloric acid, hydrobromic acid, hydroiodic acid, sulfuric acid, nitric acid and phosphoric acid or with an organic acid such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid or with an acidic amino acid such as aspartic acid and glutamic acid and salts with an inorganic base such as sodium, potassium, magnesium, calcium and aluminum, an organic base such as methylamine, ethylamine and ethanolamine, a basic amino acid such as lysine and ornithine and an ammonium salt.

In addition, hydrates, pharmaceutically acceptable various solvates and polymorphism of the compound (I) are also included in this invention. Incidentally, it goes without saying that this invention is not limited to the compounds mentioned in the following Examples but includes all of the diazepan derivatives represented by the general formula (I) and pharmaceutically acceptable salts thereof.

Incidentally, the compound of this invention includes all of the so-called prodrugs, i.e., the compounds which can be converted to the compound represented by the general formula (I) or a salt thereof by metabolism in vivo. Examples of the group which forms the prodrugs of the compound of this invention are those mentioned in *Prog. Med.* 5: 2157–2161 (1985) and those mentioned in "Iyakuhin no Kaihatsu" (Development of Pharmaceuticals) published by Hirokawa Shoten in 1990, Vol. 7, "Molecular Design", pages 163–198.

(Production Methods)

Typical production methods of the compound of this invention will be illustrated as hereunder.

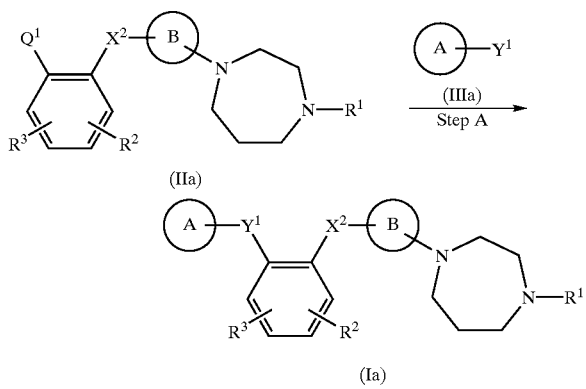

(In the formulae, A, B, $R^1$, $R^2$, $R^3$ and $X^2$ have the same meanings as defined already; $Q^1$ and $W^1$ are that, when $Q^1$ is —$NHR^4$, $W^1$ is —COOH while, when $Q^1$ is —COOH, $W^1$ is —$NHR^4$; $Y^1$ is —C(=O)—$NR^4$— or —$NR^4$—C (=O)—; and $R^4$ has the same meanings as defined already.)

Step A

This is a reaction to synthesize the compound (Ia) in which an amine and a carboxylic acid comprising a combination of the compound (IIa) and the compound (IIIa) are reacted preferably in the presence of a condensing agent. This reaction may be carried out according to the usual acylation reaction.

Examples of the condensing agent which is used advantageously are N,N-dicyclohexylcarbodiimide (DCC), 1-ethyl-3-[3-(N,N-dimethylamino)propyl]carbodiimide, carbonyldiimidazole, diphenylphosphoryl azide (DPPA) and diethylphosphoryl cyanide.

It is also possible that a carboxylic acid is made into the active derivatives of the corresponding carboxylic acid and then condensed with an amine.

Examples of the active derivative of the carboxylic acid used are active ester prepared by the reaction with a compound of a phenol type such as p-nitrophenol or an N-hydroxyamine type such as 1-hydroxysuccinimide and 1-hydroxybenzotriazole, carbonic acid monoalkyl ester, mixed acid anhydride prepared by the reaction with organic acid and a phosphoric acid type mixed acid anhydride prepared by the reaction with phosphoryl chloride and N-methylmorpholine; acid azide prepared by the reaction of an ester with hydrazine and alkyl nitrite; acid halides such as acid chloride and acid bromide; and acid anhydride of a symmetric type. Usually, the above reaction is carried out in a solvent from with cooling to at room temperature although, in some cases, it is to be carried out under an anhydrous condition depending upon the type of the acylation reaction.

Examples of the applicable solvent are inert solvents which do not participate in the reaction such as water, ethanol, methanol, dimethylformamide, dioxane, tetrahydrofuran, ether, dichloroethane, dichloromethane, chloroform, carbon tetrachloride, dimethoxymethane, dimethoxyethane, ethyl acetate, benzene, acetonitrile and dimethyl sulfoxide and a mixed solvent thereof and an appropriate selection depending upon the applied method is preferred.

In addition, depending upon the applied method, there are some cases where the reaction smoothly proceeds in the presence of a base or using such a base as a solvent where the base is sodium carbonate, potassium carbonate, sodium ethoxide, 1,8-diazabicyclo[5.4.0]undec-7-ene (DBU), N-methylmorpholine, triethylamine, trimethylamine, pyridine, sodium hydride, butyl lithium, sodium amide, or the like.

Further, any methods other than above-described reactions may be employed so far as they are a reaction for forming an amide linkage.

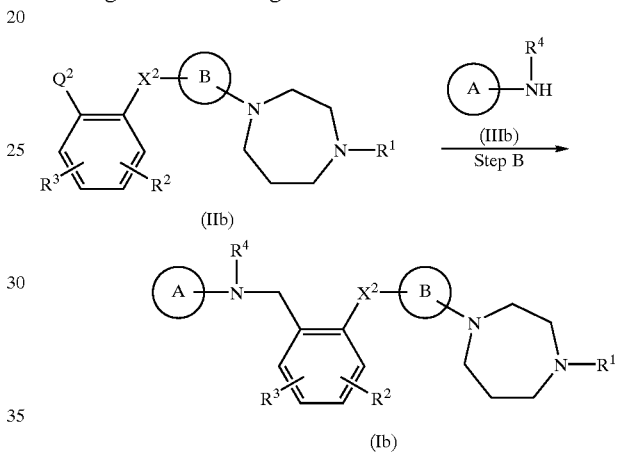

(In the formulae, A, B, $R^1$, $R^2$, $R^3$, $R^4$ and $X^2$ have the same meanings as defined already; and $Q^2$ is —CHO or —$CH_2$-leaving group. Examples of the leaving group include halogen atom, —O—($SO_2$)-alkyl and —O—($SO_2$)-aryl.)

Step B

This is a reaction to synthesize the compound (Ib) in which an aldehyde and an amine, or a —$CH_2$-leaving group-containing compound and an amine, comprising a combination of the compound (IIb) and the compound (IIIb) are condensed.

In the case of the combination of the aldehyde and the amine, the reaction may be carried out according to a usual reductive amination reaction in the presence of a reducing agent.

As the reducing agent, sodium borohydride, sodium cyanoborohydride, sodium triacetoxyborohydride, borane-trimethylamine complex and the like can be suitably used. Further, catalytic hydrogenation may be carried out at atmospheric pressure or under an elevated pressure in the presence of a catalyst such as palladium-carbon and platinum oxide. The reaction is carried out under cooling or heating in a solvent that does not participate in the reaction. In addition, depending upon the applied method, there are some cases where the reaction smoothly proceeds in the presence of an acid such as acetic acid, toluenesulfonic acid and sulfuric acid or using such an acid as a solvent.

In the case of the combination of the —$CH_2$-leaving group-containing compound and the amine, the reaction may be carried out according to a usual N-alkylation reaction.

The reaction is carried out under cooling or heating in a solvent that does not participate in the reaction. In addition, depending upon the applied method, there are some cases where the reaction smoothly proceeds in the presence of the base as described above or using such a base as a solvent.

Further, any methods other than above-described reactions may be employed so far as they are a reaction for forming an —NR$^4$—CH$_2$-linkage.

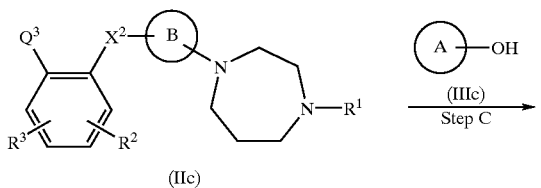

(IIc)

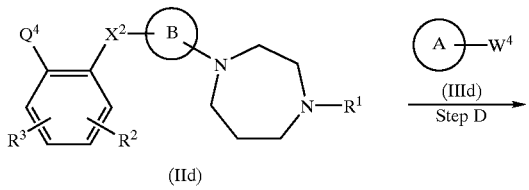

(Ic)

(In the formulae, A, B, R$^1$, R$^2$, R$^3$ and X$^2$ have the same meanings as defined already; and Q$^3$ is —CH$_2$-leaving group. Examples of the leaving group include halogen atom, —O—(SO$_2$)-alkyl and —O—(SO$_2$)-aryl.)

Step C

This is a reaction to synthesize the compound (Ic) in which a —CH$_2$-leaving group-containing compound and an alcohol comprising a combination of the compound (IIc) and the compound (IIIc) are condensed. The reaction may be carried out according to a usual N-alkylation reaction.

The reaction is carried out under cooling or heating in a solvent that does not participate in the reaction. In addition, depending upon the applied method, there are some cases where the reaction smoothly proceeds in the presence of the base as described above or using such a base as a solvent.

Further, any methods other than above-described reactions may be employed so far as they are a reaction for forming an ether linkage.

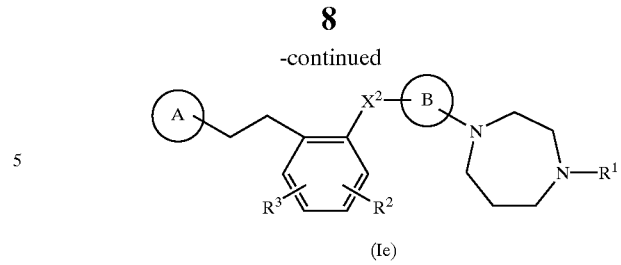

(IId)

(Id)

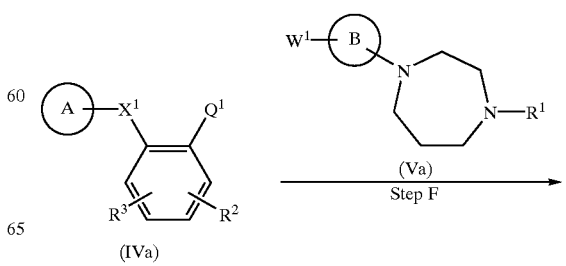

(Ie)

(In the formulae, A, B, R$^1$, R$^2$, R$^3$ and X$^2$ have the same meanings as defined already; and Q$^4$ and W$^4$ are that, when Q$^4$ is —CHO, W$^4$ is a phosphonium salt such as —CH$_2$—P$^+$Ph$_3$Br$^-$, a phosphorous diester such as —CH$_2$—P(=O)(—OEt$_2$), or a phosphine oxide such as —CH$_2$—P(=O)(-Ph)$_2$ while, when W$^4$ is —CHO, Q$^4$ is a phosphonium salt such as —CH$_2$—P$^+$Ph$_3$Br$^-$, a phosphorous diester such as —CH$_2$—P(=O)(—OEt$_2$), or a phosphine oxide such as —CH$_2$—P(=O)(-Ph)$_2$.)

Step D

This is a reaction to synthesize the compound (Id) in which an aldehyde and a phosphonium salt, a phosphorous diester or a phosphine oxide comprising a combination of the compound (IId) and the compound (IIId) are reacted in the presence of the base as described above. The reaction may be carried out according to a usual Wittig reaction or Wittig-Horner reaction.

The reaction is carried out under cooling or heating in a solvent that does not participate in the reaction. Depending upon the applied method, an intermediate ylide as isolated may be reacted with the aldehyde.

Further, any methods other than above-described reactions may be employed so far as they are a reaction for forming a carbon-carbon double bond.

Step E

This is a reaction to synthesize the compound (Ie) through a reduction reaction of the compound (Id). The reaction may be carried out according to a usual hydrogenation reaction using a catalyst.

The reaction is carried out in a hydrogen atmosphere under cooling or heating in a solvent that does not participate in the reaction. Depending upon the applied method, the reaction is carried out under an elevated pressure. Examples of the catalyst that is used include palladium-carbon (Pd—C), platinum oxide, Raney nickel, chlorotriphenylphosphine rhodium (Whilkinson's catalyst) and nickel borohydride. In addition, the reaction may be carried out using a hydrogen source such as ammonium formate, sodium phosphinate and hydrazine in place of using the hydrogen atmosphere.

Further, any methods other than above-described reactions may be employed so far as they are a reaction for reducing the double bond.

Moreover, any methods may be employed even not via the compound (Id) so far as they are a reaction for forming a —CH$_2$—CH$_2$— linkage.

(IVa)

-continued

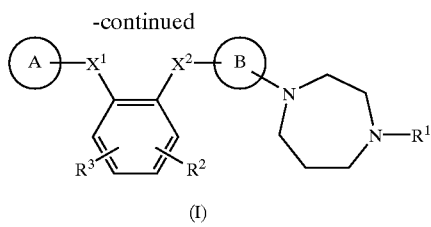

(I)

(In the formulae, A, B, $R^1$, $R^2$, $R^3$, $X^1$, $X^2$, $Q^1$ and $W^1$ have the same meanings as defined already.)

Step F

This is a reaction to synthesize the compound (I) in which a carboxylic acid and an amine comprising a combination of the compound (IVa) and the compound (Va) are reacted. The reaction is carried out in the same manner as in the step A.

Compounds (I) of this invention wherein $R^1$ is hydrogen can also be obtained through the above-described hydrogenation reaction or the like, using a compound (I) of this invention where $R^1$ is benzyl.

Further, compounds (I) of this invention wherein $R^1$ is one other than hydrogen atom can also be obtained through the above-described usual reductive amination or N-alkylation or the like, using a compound (I) of this invention wherein $R^1$ is hydrogen atom.

Moreover, compounds (I) of this invention wherein $R^2$ is —OH can also be obtained by protecting its hydroxyl group by a protective group for phenol to synthesize a compound and then cleaving the protective group in a method suitable for cleavage. With regard to the protective group for phenol, there is no particular limitation so far as it is a group which is usually used for protection of phenol, and its examples include optionally substituted lower alkyl, aralkyl, tri(lower alkyl)silyl, lower alkylcarbonyl, lower alkyloxycarbonyl and sulfonyl. "Aralkyl" means a group where hydrogen atom of the above-described alkyl is substituted with aryl, and its specific examples include benzyl and phenylethyl.

It is also possible to obtain compounds wherein $R^2$ is —O-lower alkyl, —O-lower alkylene-OH, —O-lower alkylene-COOH or —O-lower alkylene-COO-lower alkyl, through the above-described usual —O-alkylation or the like using a compound (I) of this invention wherein $R^2$ is OH. Further, it is possible to obtain the compounds wherein $R^2$ is —O—$SO_2$—OH by sulfone oxidation of a compound (I) of this invention wherein R2 is OH using a trimethylamine-sulfur trioxide complex or the like. Moreover, in the case where $R^2$ contains ester group, it is possible to obtain the compounds wherein $R^2$ contains carboxyl group through hydrolysis under an acidic condition of an aqueous solution of hydrochloric acid or the like, or under a basic condition of an aqueous solution of sodium hydroxide or the like.

It is also possible to obtain compounds (I) of this invention wherein the ring A contains hydroxyamidino group or amidino group using a compound (I) of this invention wherein the ring A contains nitrile group.

The synthesis of compounds (I) of this invention wherein the ring A contains hydroxyamidino group can be carried out by reacting a compound (I) of this invention wherein the ring A contains nitrile group with hydroxylamine. The reaction is carried out under cooling or heating in a solvent that does not participate in the reaction. In addition, depending upon the applied method, there are some cases where the reaction smoothly proceeds in the presence of the base as described above or using such a base as a solvent.

The synthesis of compounds (I) of this invention wherein the ring A contains amidino group includes the following methods (i) to (iV).

(i) Method in Which a Nitrile is Converted into an Imidate, which is then Condensed with an Amine A compound (I) of this invention wherein the ring A contains nitrile group is reacted with an alcohol such as methanol and ethanol at −40° C. to 0° C. in the presence of hydrogen chloride gas to form an imidate, which is then reacted with an amine or amine salt such as ammonia, ammonium carbonate, ammonium chloride and ammonium acetate. As the solvent, the above-described solvent that does not participate in the reaction can be used.

(ii) Method in Which a Nitrile is Converted into a Thioimidate Via a Thioamide, which is then Condensed with an Mine A compound (I) of this invention wherein the ring A contains nitrile group is reacted with hydrogen sulfide in the presence of an organic base such as methylamine, triethylamine, pyridine and picoline, or a compound (I) of this invention wherein the ring A contains nitrile group is reacted with o,o-diethyl dithiophosphate, to form a thioamide.

Subsequently, the thioamide is reacted with a lower alkyl halide such as methyl iodide and ethyl iodide to form a thioimidate, which is then reacted with an amine or amine salt such as ammonia, ammonium carbonate, ammonium chloride and ammonium acetate. As the solvent, the above-described solvent that does not participate in the reaction can be used.

(iii) Method in which an Amine, Amine Salt, Metal Amide or Grignard Reagent Is Added Directly to a Nitrile A reagent such as ammonia, ammonium chloride and ammonia, ammonium thiocyanate, alkylammonium thiocyanate, $NaNH_2$ and $(CH_3)_2NMgBr$ is added directly to a compound (I) of this invention wherein the ring A contains nitrile group. As the solvent, the above-described solvent that does not participate in the reaction can be used. Further, the reaction can be carried out without using a solvent.

(iv) Method for Reducing Hydroxyamidino Group

A compound (I) of this invention wherein the ring A contains hydroxyamidino group is subjected to hydrogenation as described above directly. Alternatively, it is exerted with acetic anhydride or trifluoroacetic anhydride in the presence of a solvent such as acetic acid or trifluoroacetic acid and then subjected to hydrogenation as described above. Thus, the hydroxyamidino group can be reduced.

Further, any methods other than the above-described reactions may be employed so far as they are a reaction for forming an amidino group.

The compound represented by the general formula (I) may also be manufactured by an optional combination of the steps which can be usually adopted by the persons skilled in the art such as known alkylation, acylation, oxidation, reduction and hydrolysis. In addition, the method shown by the following reaction schemes is particularly effective for the synthesis of the compound represented by the general formula (I).

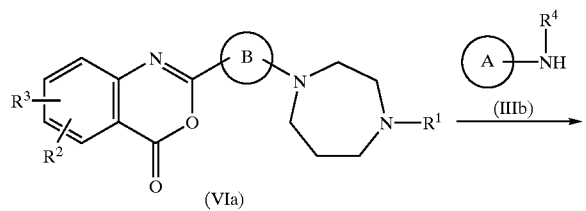

(VIa) (IIIb)

-continued

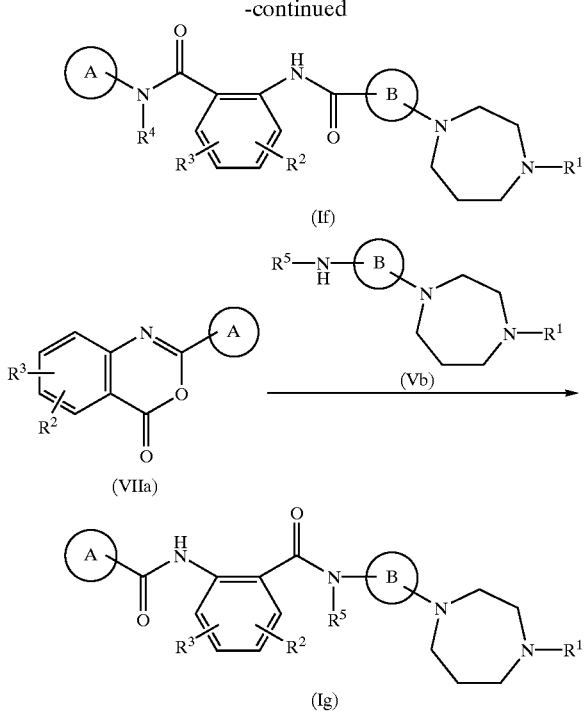

(In the formulae, A, B, $R^1$, $R^2$, $R^3$, $R^4$ and $R^5$ have the same meanings as defined already.)

This is a reaction in which the compound (VIa) and the amine (IIIb), or the compound (VIIa) and the amine (Vb), are reacted to form an amide linkage to give the compound (If) or the compound (Ig) and that is carried out in the above-mentioned inert solvent at room temperature or under heating. In addition, depending upon the applied method, there are some cases where the reaction smoothly proceeds in the presence of a base or using such a base as a solvent where the base is N-methylmorpholine, triethylamine, trimethylamine, pyridine, sodium hydride, potassium tert-butoxide, butyl lithium, sodium amide, or the like.

(Production Methods for the Starting Compounds)

As hereunder, typical production methods for the starting compounds of the compound (I) of this invention will be illustrated.

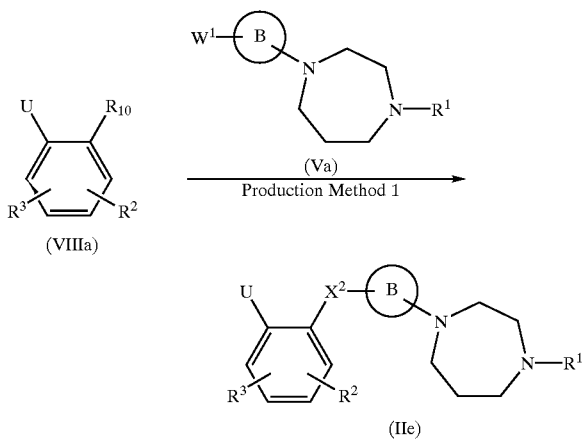

(In the formulae, B, $R^1$, $R^2$, $R^3$, $Q^1$, $W^1$ and $X^2$ have the same meanings as defined already; U is —COOH, —NHR$^5$, —CH$_2$— leaving group, —CHO, a phosphonium salt such as —CH$_2$—P$^+$Ph$_3$Br$^-$, a phosphorous diester such as —CH$_2$—P(=O)(—OEt$_2$), or a phosphine oxide such as —CH$_2$—P(=O)(-Ph)$_2$; and R$^5$ has the same meanings as defined already.)

Production Method 1

This is a reaction in which a carboxylic acid and an amine comprising a combination of the compound (VIIIa) and the compound (Va) are condensed to form an amide linkage. This reaction is carried out in the same manner as in the above-mentioned step A.

Further, in the case where in the compound (IIe), U means —CH$_2$-leaving group, it is possible to obtain compounds wherein U is —CHO by oxidation reaction using 4-methylmorpholine N-oxide or the like. Also, it is possible to obtain compounds wherein U is a phosphonium salt such as —CH$_2$—P$^+$Ph$_3$Br$^-$ by reaction with an organophosphorus compound such as triphenylphosphine.

The compound represented by the general formula (IIe) may also be manufactured by an optional combination of the steps which can be usually adopted by the persons skilled in the art such as known alkylation, acylation, oxidation, reduction and hydrolysis. For example, after obtaining a compound wherein —NO$_2$ is present in a site corresponding to U, the compound is subjected to a reduction reaction such as hydrogenation as described above, whereby a compound wherein U is NH$_2$ can be obtained. Further, after obtaining a compound wherein ester group is present in a site corresponding to U, the compound is subjected to hydrolysis under an acidic condition using an aqueous solution of hydrochloric acid or the like, or under an alkaline condition using sodium hydroxide or the like, whereby a compound wherein U is —COOH can be obtained. Moreover, it is possible to obtain a compound wherein U is —NHR$^5$ by using a compound wherein a site corresponding to U is protected by t-butoxycarbonyl group, benzyl group or the like and cleaving the respective protective groups in a method suitable for cleaving the protective groups such as an acidic condition using trifluoroacetic acid or the like and a reducing condition such as hydrogenation as described above.

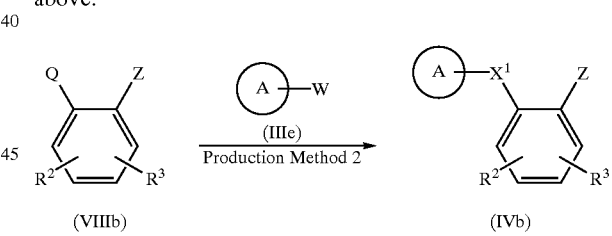

(In the formulae, A, $R^2$, $R^3$ and $X^1$ have the same meanings as defined already. Z means —COOH or —NHR$^5$. Q and W are that, when Q means $Q^1$, W means $W^1$; when Q means $Q^2$, W means —NHR$^4$; when Q means $Q^3$, W means —OH; and when Q means $Q^4$, W means $W^4$, respectively. $Q^1$, $Q^2$, $Q^3$, $Q^4$, $W^1$, $W^4$ and $R^4$ have the same meanings as defined already.)

Production Method 2

This is a reaction to synthesize the compound (IVb) in which, when Q means $Q^1$, and W means $W^1$, a carboxylic acid and an amine comprising a combination of the compound (VIIIb) and the compound (IIIe) are reacted. The reaction can be carried out in the same manner as in the step A.

This is a reaction to synthesize the compound (IVb) in which, when Q means $Q^2$, and W means —NHR$^4$, an aldehyde and an amine, or a —CH$_2$-leaving group-containing compound and an amine, comprising a combination of the compound (VIIIb) and the compound (IIIe) are condensed. The reaction can be carried out in the same manner as in the step B.

This is a reaction to synthesize the compound (IVb) in which, when Q means $Q^3$, and W means —OH, a —$CH_2$- leaving group-containing compound and an alcohol comprising a combination of the compound (VIIIb) and the compound (IIIe) are condensed. The reaction can be carried out in the same manner as in the step C.

This is a reaction to synthesize the compound (IVb) in which, when Q means $Q^4$, and W means $W^4$, an aldehydde and a phosphonium salt, a phosphorous diester or a phosphine oxide comprising a combination of the compound (VIIIb) and the compound (IIIe) are condensed. The reaction can be carried out in the same manner as in the step D.

In addition, the compound represented by the general formula (IVb) may also be manufactured by an optional combination of the steps which can be usually adopted by the persons skilled in the art such as known alkylation, acylation, oxidation, reduction and hydrolysis. For example, after obtaining a compound wherein —$NO_2$ is present in a site corresponding to Z, the compound is subjected to a reduction reaction such as hydrogenation as described above, whereby a compound wherein, Z is —$NH_2$ can be obtained. Further, after obtaining a compound wherein ester group is present in a site corresponding to Z, the compound is subjected to hydrolysis under an acidic condition using an aqueous solution of hydrochloric acid or the like, or under an alkaline condition using sodium hydroxide or the like, whereby a compound wherein Z is —COOH can be obtained. Moreover, it is possible to obtain a compound wherein Z is —$NHR^5$ by using a compound wherein a site corresponding to Z is protected by t-butoxycarbonyl group, benzyl group or the like and cleaving the respective protective groups in a method suitable for cleaving the protective groups such as an acidic condition using trifluoroacetic acid or the like and a reducing condition such as hydrogenation as described above.

In addition, the method shown in the following reaction scheme is particularly effective for synthesizing the compounds represented by the general formulae (IIf) and (IVc).

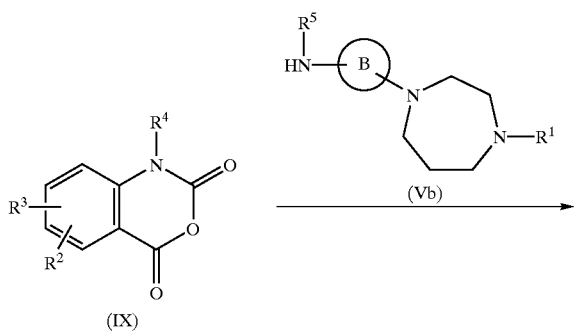

(IX)

(Vb)

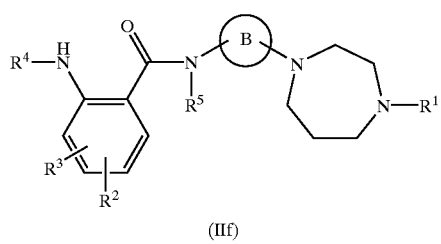

(IIf)

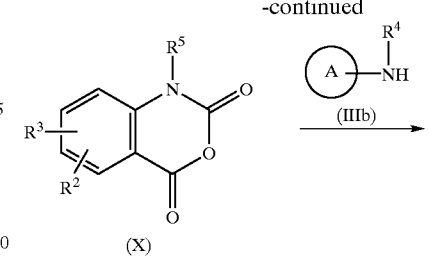

(X)

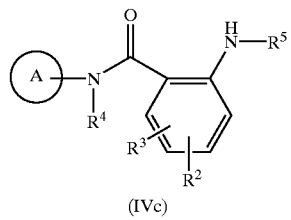

(IIIb)

-continued (IVc)

(In the formulae, A, B, $R^1$, $R^2$, $R^3$, $R^4$ and $R^5$ have the same meanings as defined already.)

This is a reaction where an amide linkage is formed by the reaction of the compound (IX) with the amine (Va), or the compound (X) with the amine (IIIb), to give the compound (IIf) or compound (IVc) and that is carried out in the above-mentioned inert solvent at room temperature or under heating. In addition, depending upon the applied method, there are some cases where the reaction smoothly proceeds in the presence of a base or using such a base as a solvent in which the base is N-methylmorpholine, triethylamine, trimethylamine, pyridine, sodium hydride, potassium tert-butoxide, butyl lithium, sodium amide, or the like.

The compound of this invention produced in this way can be isolated and purified by known techniques such as extraction, precipitation, separation chromatography, fractionating crystallization, recrystallization. Also, the compound of this invention can be made into desired salts by subjecting it to a usual salt forming reaction.

In addition, the compound of this invention may exist in the form of optical isomers when it has asymmetric carbons. Those optical isomers can be separated in the usual method by fractionating crystallization in which an isomer is recrystallized together with an appropriate salt or by column chromatography or the like.

Industrial Applicability

The compound of this invention shows a potent anticoagulation action by inhibiting the activated blood coagulation factor X in s specific manner. Accordingly, the compound is useful as a blood coagulation inhibitor or a drug for use in the prevention and the treatment of diseases which are induced by thrombus or embolus.

Examples of such diseases include cerebrovascular disorders such as cerebral infarction, cerebral thrombosis, cerebral embolism, transient cerebral ischemic attack (TIA), subarachnoid hemorrhage (vascular twitching) and the like, ischemic heart diseases such as acute or chronic myocardial infarction, unstable angina, coronary artery thrombolysis and the like, pulmonary vascular disorders such as pulmonary thrombosis, pulmonary embolism and the like, and various vascular disorders such as peripheral arterial obstruction, deep vein thrombosis, disseminated intravascular coagulation syndrome, thrombus formation after artificial blood vessel operation or after artificial valve replacement, re-occlusion and re-stricture after coronary artery by-pass operation, re-occlusion and re-stricture after PTCA (percutaneous transluminal coronary angioplasty) or PTCR (percutaneous transluminal coronary re-canalization) operation and thrombus formation at the time of extracorporeal circulation.

In addition, a possibility has been suggested on the use of the compound having an activated blood coagulation factor X inhibiting action as a drug for use in the prevention and the treatment of influenza virus infection based on the activity to inhibit the growth of influenza virus (Japanese Patent Laid-Open No. 227971/1994) and, therefore, the compound of this invention is also expected to have the same effect.

The excellent activity of the compound of this invention to inhibit the activated blood coagulation factor X has been confirmed by the following tests.

1) Test on Measurement of Coagulation Time by Human Activated Blood Coagulation Factor X To 90 μl of human blood plasma were added 10 μl of a drug or a physiological saline and 50 μl of human factor Xa (Enzyme Research Labs), incubation was carried out at 37° C. for 3 minutes, 100 μl of 20 mM $CaCl_2$ previously warmed at 37° C. were added and the time until coagulation was measured by a coagulo-meter (KC10 of Amelung). With regard to the human blood plasma, each 45 ml of blood were collected from vein of elbow of six healthy persons using a syringe in which 5 ml of 3.8% sodium citrate were contained and centrifuged at 4° C. for 15 minutes at 3,000 rpm and the separated blood plasma was pooled and frozen, then thawed before use. With regard to the human factor Xa, the concentration by which the coagulation time when a physiological saline (control) was added was about 30 to 40 seconds was selected. A $CT_2$ value (concentration by which the coagulation time is prolonged to an extent of 2-fold) was determined by plotting the drug concentrations and relative value (fold) of the coagulation time to the control, followed by subjecting to linear regression. The results are shown in the following Table 1.

2) Test on Measurement of Coagulation Time by Bovine Thrombin

To 50 μl of human blood plasma was added 50 μl of a drug or a physiological saline, incubation was carried out at 37° C. for 3 minutes, 50 μl of thrombin (500 units of Thrombin (derived from bovine; Mochida Pharmaceutical) previously warmed at 37° C. was added and the time until coagulation was measured by a coagulo-meter (KC10 of Amelung). With regard to the human blood plasma, each 45 ml of blood was collected from vein of elbow of six healthy persons using a syringe in which 5 ml of 3.8% sodium citrate was contained and centrifuged at 4° C. for 15 minutes at 3,000 rpm and the separated blood plasma was pooled and frozen, then thawed before use. With regard to the thrombin, the concentration by which the coagulation time when a physiological saline (control) was added was about 20 seconds was selected. A $CT_2$ value (concentration by which the coagulation time is prolonged to an extent of 2-fold) was determined by plotting the drug concentrations and relative value (fold) of the coagulation time to the control, followed by subjecting to linear regression. The results are shown in the following Table 1.

TABLE 1

| | Compound | Test on measurement of coagulation time by human activated blood coagulation factor X($CT_2$) (μM) | Test on measurement of coagulation time by bovine thrombin ($CT_2$) (μM) |
|---|---|---|---|
| Compounds of Examples | Example 5 | 0.10 | >100 |
| | Example 9 | 1.71 | >100 |
| | Example 11 | 1.33 | >100 |
| | Example 32 | 1.41 | >100 |
| | Example 39 | 1.53 | >100 |
| Control Compounds | Control 1 | 17.0 | >100 |
| | Control 2 | 11.3 | — |

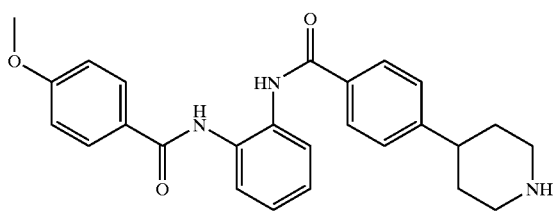

(Control 1)

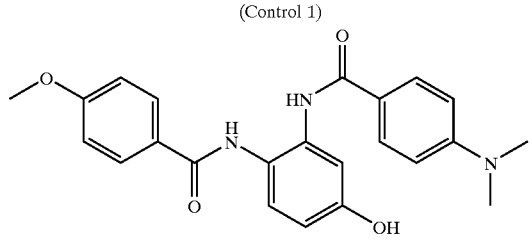

(Control 2)

(Example 42 of WO 99/00121) (Example 198 of WO 99/00121)

3) Test on Measurement of Enzyme Inhibition by Synthetic Substrate Method

To a 96-well microplate were added 80 μl of a reaction buffer (pH 8.4), 15 μl of a drug and 30 μl of 2 mM synthetic substrate S-2222 (Chromogenix), then 25 μl of 0.025 U/ml of human activated blood coagulation factor X (Factor Xa; Enzyme Research Labs) was added, the reaction was carried out at 37° C. for 10 minutes, changes in absorbance 405 nm were measured by a Bio-Rad Model 3550 and $IC_{50}$ was calculated. The compound of Example 1 exhibited an $IC_{50}$ of 10 nM or less.

As a result of the measurements of the above 1), 2) and 3), it was confirmed that the compound of this invention inhibits human activated blood coagulation factor X in a specific manner and shows a potent anticoagulation action to blood. For example, the compounds shown in Examples 5, 9, 11, 32 and 39 of this invention were confirmed to clearly extend the coagulation time at low concentration showing an excellent anti-blood coagulation action as compared with Example 42 (control 1) and Example 198 (control 2) of WO 99/00121.

4) Test on ex vivo Measurement of Coagulation Time in Mice (Oral Administration)

A drug which was dissolved or suspended in 0.5% methylcellulose was compulsorily administered po (100 mg/kg) via an oral gavage to a male ICR mouse (20–30 g; Japan SLC) fasted for 12 hours or longer and, after 30 minutes and 2 hours, 0.9 ml of blood was collected under anesthetization with diethyl ether from inferior vena cava by a syringe containing 100 μl of 3.8% sodium citrate and blood plasma was separated by means of centrifugal treatment of 3,000 rpm for 10 minutes. Using the resulting blood plasma, extrinsic coagulation time (PT) and intrinsic coagulation time (APTT) were measured in accordance with the following methods a) and b).

a) Extrinsic Coagulation Time (PT)

Ortho Brain Thromboplastin (54 mg/vial; a freeze-dried preparation; Ortho-Clinical Diagnostics) was dissolved in 2.5 ml of Milli-Q water and preliminarily warmed at 37° C. The above-separated blood plasma (50 μl) was warmed at 37° C. for 1 minute, 50 μl of the above-mentioned thromboplastin solution was added and the coagulation time was measured. Amelung KC10A was used for the measurement of the coagulation time.

b) Intrinsic Coagulation Time (APTT)

To 50 μl of the above blood plasma was added 50 μl of Hemoliance Thrombosil I (DIA-IATRON), the mixture was warmed at 37° C. for 3 minutes, 50 μl of a 20 mM $CaCl_2$ solution previously warmed at 37° C. were added and the coagulation time was measured. KC10A manufactured by Amelung was used for the measurement of the coagulation time.

Dose dependency of and time-course changes in the anticoagulation action were also examined by changing the administration dose or the blood collection time.

5) Test on ex vivo Measurement of Coagulation Time in Cynomolgus Monkeys (Oral Administration)

A drug (5 mg/ml) which was dissolved (suspended) in 0.5% methylcellulose was compulsorily administered po at a dose of 10 mg/kg (2 ml/kg) via an oral gavage after blood collection before the administration of the drug to a male cynomolgus monkeys (body weight around 4 kg) fasted for 12 hours or longer and, after 1, 2, 4, 6 and 8 hours, 2 ml of blood was collected from femoral vein using 1/10 volume of 3.8% sodium citrate and blood plasma was separated by means of centrifugal treatment of 3,000 rpm for 10 minutes. Using the resulting blood plasma, extrinsic coagulation time (PT) and intrinsic coagulation time (APTT) were measured in accordance with the above methods a) and b). Incidentally, the experiment was carried out under non-anesthetization.

As a result of the tests of 4) and 5), the compound of this invention was confirmed to have an action of prolongation the coagulation time by an oral administration as well. The compound shown in Example 3 exhibited a twice or more action of prolongation the coagulation time in terms of PT and APTT in both of the tests of 4) and 5) as compared with the control (plasma without administration of a drug).

The pharmaceutical composition which contains one or more compounds of this invention represented by the general formula (I) or pharmaceutically acceptable salts thereof as the active ingredient is prepared into tablets, diluted powders, fine granules, granules, capsules, pills, solutions, injections, suppositories, ointments, plasters and the like using commonly used pharmaceutical carriers, fillers and other additives and administered either orally or parenterally.

Clinical dose of the compound of this invention in human is optionally decided by taking symptoms, body weight, age, sex and the like of each patient to be treated into consideration and, usually, it is 0.1 to 500 mg by oral administration or 0.01 to 100 mg by parenteral administration per day per adult where the daily dose is divided into one to several times per day. Since the dose varies under various conditions, a smaller dose than the above range may be sufficient in some cases.

The solid composition for use in the oral administration according to this invention is used in the form of tablets, diluted powders, granules and the like. In such a solid composition, one or more active substances are mixed with at least one inert diluent such as lactose, mannitol, glucose, hydroxypropyl cellulose, microcrystalline cellulose, starch, polyvinylpyrrolidone, metasilicic acid or magnesium aluminate. In the usual manner, the composition may contain additives other than the inert diluent, such as a lubricant (e.g., magnesium stearate), a disintegrating agent (e.g., calcium cellulose glycolate), a stabilizing agent (e.g., lactose) and a solubilizing agent or a solubilizing aid (e.g., glutamic acid and aspartic acid). If necessary, tablets or pills may be coated with a film of a gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a commonly used inert diluent such as pure water or ethyl alcohol. In addition to the inert diluent, this composition may also contain auxiliary agents such as a solubilizing agent or a solubilizing aid, a moistening agent, a suspending agent and the like, as well as sweeteners, flavors, aromas and antiseptics.

The injections for parenteral administration includes aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, a vegetable oil (e.g., olive oil), an alcohol (e.g., ethyl alcohol), Polysorbate 80 (a trade name) and the like.

Such a composition may further contain additive agents such as isotonic agent, an antiseptic agent, a moistening agent, an emulsifying agent, a dispersing agent, a stabilizing agent (e.g., lactose) and a solubilizing agent or a solubilizing aid. Those compositions are sterilized by filtering through a bacteria retaining filter, blending of a germicide or irradiation. Alternatively, they may be used by firstly making into sterile solid compositions and dissolving them in sterile water or a sterile solvent for injection prior to their use.

BEST MODE FOR CARRYING OUT THE INVENTION

The following description specifically illustrates the production method of the compounds of this invention with reference to the production examples of the compounds of this invention. In this connection, since novel compounds are included in the starting material compounds for the compounds of this invention, production methods of them are also described as the Referential Examples.

Referential Example 1

Ethyl 4-bromomethyl-3-nitrobenzoate (26.00 g) was dissolved in 90 ml of acetonitrile, then 7.97 g of 3-aminobenzonitrile and 12.44 g of potassium carbonate were added and the mixture was stirred at 70° C. for 3 hours. The reaction solution was cooled to room temperature, and after filtration, the mother liquor was concentrated in vacuo. Ethyl acetate was added to the resulting residue. The mixture was washed with a 1N aqueous solution of hydrochloric acid and a saturated aqueous solution of sodium bicarbonate, dried over anhydrous magnesium sulfate and concentrated in vacuo. The resulting residue was purified by silica gel column chromatography using hexane-ethyl acetate (80:20 to 75:25) as an eluting solvent to give 12.06 g of ethyl 4-[(3-cyanophenylamino)methyl]-3-nitrobenzoate.

Referential Example 2

Ethyl 4-[(3-cyanophenylamino)methyl]-3-nitrobenzoate (5.79 g) was dissolved in 50 ml of ethanol, then 50 ml of purified water, 0.96 g of ammonium chloride and 4.97 g of iron powder were added and the mixture was refluxed under heating for 40 minutes. The reaction solution was filtered through Celite and concentrated in vacuo. Ethyl acetate was added to the resulting residue. The mixture was washed with a saturated aqueous solution of sodium bicarbonate and a saturated aqueous solution of sodium chloride, dried over anhydrous magnesium sulfate, concentrated in vacuo and dried to give 5.71 g of ethyl 3-amino-4-[(3-cyanophenylamino)methyl]benzoate.

Referential Example 3

Ethyl 4-bromomethyl-3-nitrobenzoate (46.11 g) was dissolved in 500 ml of acetonitrile, then 20 g of 4-methylmorpholine-N-oxide was added and the mixture was stirred at room temperature for 80 minutes. The reaction solution was concentrated in vacuo, water was added and the mixture was extracted with chloroform. The organic layer was washed with a saturate aqueous solution of sodium chloride, dried over magnesium sulfate and concentrated in vacuo. The resulting residue was purified by silica gel column chromatography using hexane-ethyl acetate (4:1) as an eluting solvent to give 10.723 g of ethyl 4-formyl-3-nitrobenzoate.

Referential Example 4

Ethyl 4-formyl-3-nitrobenzoate (5.81 g) was dissolved in 70 ml of toluene, then 2.1 ml of 1,8-diazabicyclo[5.4.0]-undec-7-ene and the mixture was stirred at 80° C. for one hour. To the reaction solution, 2.69 g of 3-[(1,1,1-triphenylphosphonio)methyl]benzonitrile bromide was added, and the mixture was stirred at 80° C. for 24 hours. Insoluble matters were filtered out and the filtrate was concentrated in vacuo. The resulting residue was purified by silica gel column chromatography using hexane-ethyl acetate (10:1) as an eluting solvent. The resulting intermediate (3.1 g) was dissolved in a mixed solvent of 50 ml of ethanol and 10 ml of tetrahydrofuran, then 1 g of a palladium oxide-barium sulfate complex was added and the mixture was stirred in a hydrogen atmosphere at room temperature for 3 days. The reaction solution was filtered through Celite and the filtrate was concentrated in vacuo. The resulting residue was purified by silica gel column chromatography using hexane-ethyl acetate (2:1) as an eluting solvent to give 2.35 g of ethyl 3-amino-4-[2-(3-cyanophenyl)ethyl]benzoate.

Referential Example 5

3-Hydroxy-2-nitrobenzoic acid (1.83 g) was dissolved in 50 ml of N,N-dimethylformamide, then 1.23 g of 4-methoxyaniline, 2.50 g of 1-ethyl-3-dimethylaminopropylcarbodiimide hydrochloride, 1.35 g of 1-hydroxybenzotriazole and 1.81 ml of triethylamine were added and the mixture was stirred at room temperature for 66 hours. The reaction solution was concentrated in vacuo, water was added and the mixture was extracted with ethyl acetate. The organic layer was washed with a saturated aqueous solution of sodium chloride, dried over magnesium sulfate and concentrated in vacuo. Chloroform was added to the resulting residue and the resulting precipitate was filtered to give 2.04 g of 3-hydroxy-4'-methoxy-2-nitrobenzanilide. The filtrate was purified by silica gel column chromatography using chloroform-methanol (98:2) as an eluting solvent, chloroform was added to the resulting crude product and the resulting precipitate was filtered to give additional 0.24 g of 3-hydroxy-4'-methoxy-2-nitrobenzanilide.

Referential Example 6

3-Hydroxy-4'-methoxy-2-nitrobenzanilide (1.15 g) was suspended in 50 ml of methanol, 300 mg of 10% palladium-carbon powder were added and the mixture was stirred in a hydrogen atmosphere at room temperature for 1 hour. The reaction solution was filtered through Celite and washed with methanol and the filtrate was concentrated in vacuo to give 966 mg of 2-amino-3-hydroxy-4'-methoxybenzanilide.

Referential Example 7

4-(4-Methyl-1,4-diazepan-1-yl)benzonitrile (18.86 g) was dissolved in 185 ml of 12N hydrochloric acid, stirred at 80° C. for 12 hours and concentrated in vacuo. Water was added, the mixture was stirred at room temperature and the resulting precipitate was filtered and washed with water. The resulting solid was dried in vacuo to give 18.25 g of 4-(4-methyl-1,4-diazepan-1-yl)benzoic acid hydrochloride.

Referential Example 8

A mixture of 16.3 g of 4-(4-methyl-1,4-diazepan-1-yl) benzoic acid hydrochloride, 0.88 g of N,N-dimethylformamide, 14.3 g of thionyl chloride and 160 ml of ethyl acetate was stirred at 40° C. for 3 hours and concentrated in vacuo. To a mixture of the resulting residue and 130 ml of acetonitrile, a solution of 8.35 g of 2-amino-3-nitrophenol, 9.52 g of pyridine and 60 ml of acetonitrile was added under ice cooling. The mixture was stirred at 5° C. or lower overnight and crystals were collected by filtration to give 21.4 g of 2-amino-3-nitrophenyl 4-(4-methyl-1,4-diazepan-1-yl)benzoate hydrochloride.

Referential Example 9

A mixture of 2.00 g of 2-amino-3-nitrophenyl 4-(4-methyl-1,4-diazepan-1-yl)benzoate hydrochloride, 995 mg of triethylamine and 20 ml of acetonitrile was stirred at 70° C. for 6 hours. A solution of 197 ml of sodium hydroxide and 2 ml of water was added, then 20 ml of water was added and the acetonitrile was distilled off under heating at atmospheric pressure. Water (10 ml) was further added and the mixture was stirred at room temperature for 14 hours. Deposited crystals were collected by filtration to give 1.57 g of 2'-hydroxy-4-(4-methyl-1,4-diazepan-1-yl)-6'-nitrobenzanilide.

Referential Example 10

A mixture of 2.14 g of 2'-hydroxy-4-(4-methyl-1,4-diazepan-1-yl)-6'-nitrobenzanilide, 43 ml of methanol and 467 mg of 10% palladium-carbon (wetting rate: 54.2%) was stirred in a hydrogen atmosphere of atmospheric pressure at 30° C. until the absorption of hydrogen had stopped. The catalyst was filtered out and the filtrate was concentrated in vacuo. The residue was purified by silica gel column chromatography using chloroform-methanol (20:1 to 10:1) to give 1.61 g of 2'-amino-6'-hydroxy-4-(4-methyl-1,4-diazepan-1-yl)benzanilide.

Referential Example 11

2-Amino-3-nitrophenol (308 mg) was dissolved in 10 ml of pyridine, then 341 mg of 4-methoxybenzoyl chloride was added at 0° C. and the mixture was stirred at room temperature for 18 hours. The reaction solution was concentrated in vacuo, 20 ml of chloroform was added to the resulting residue and the mixture was again concentrated in vacuo. This operation was further repeated three times, and the residue from which the pyridine had been removed was purified by silica gel column chromatography using chloroform as an eluting solvent to give 428 mg of 2'-hydroxy-4-methoxy-6'-nitrobenzanilide.

A compound of Referential Example 12 was synthesized in the same manner as in Referential Example 6.

Referential Example 13

3-Hydroxy-2-nitrobenzoic acid (10.5 g) was dissolved in 60 ml of N,N-dimethylformamide, then 15 ml of benzyl bromide and 19.0 g of potassium carbonate were added at 0° C. and the mixture was stirred for one night at room temperature. The reaction solution was filtered through Celite and concentrated in vacuo. Water was added to the resulting residue and the mixture was extracted with ether, washed with a saturated aqueous solution of sodium chloride and dried over anhydrous magnesium sulfate. The solvent was evaporated in vacuo to give 20.7 g of benzyl 3-benzyloxy-2-nitrobenzoate.

Referential Example 14

To 20.7 g of benzyl 3-benzyloxy-2-nitrobenzoate were added 100 ml of ethanol and 120 ml of 1N aqueous solution of sodium hydroxide and the mixture was stirred at room temperature for one night, at 60° C. for 3 hours and at 80° C. for 5 hours. After ethanol was evaporated in vacuo, the resulting aqueous solution was washed with ether and hydrochloric acid was added. The resulting precipitate was filtered and dried in vacuo to give 15.8 g of 3-benzyloxy-2-nitrobenzoic acid.

Referential Example 15

To 5.47 g of 3-benzyloxy-2-nitrobenzoic acid were added 20 ml of thionyl chloride and a few drops of N,N-dimethylformamide and the mixture was stirred at 80° C. for 30 minutes. The reaction solution was concentrated in vacuo, 35 ml of pyridine and 2.55 g of 2-amino-5-chloropyridine were added to the residue at 0° C. and the mixture was stirred at room temperature for one night. The reaction solution was concentrated in vacuo, a saturated aqueous solution of sodium bicarbonate was added to the resulting residue and the mixture was extracted with chloroform. The organic layer was dried over anhydrous magnesium sulfate, the solvent was evaporated in vacuo and the residue was subjected to an azeotropic treatment with toluene to give 7.44 g of 3-benzyloxy-N-(5-chloro-2-pyridyl)-2-nitrobenzamide.

Referential Example 16

To 7.44 g of 3-benzyloxy-N-(5-chloro-2-pyridyl)-2-nitrobenzamide were added 40 ml of trifluoroacetic acid and 3.72 g of pentamethylbenzene and the mixture was stirred at 40° C. for one night. The reaction solution was concentrated in vacuo, a saturated aqueous solution of sodium bicarbonate was added to the resulting residue to such an extent that the residue did not become alkaline and the mixture was extracted with chloroform. The organic layer was extracted with a 1N aqueous solution of sodium hydroxide and the aqueous layer was acidified by adding hydrochloric acid thereto and extracted with chloroform. The extract was dried over anhydrous magnesium sulfate, the solvent was evaporated in vacuo and 200 ml of an ethanolic suspension of Raney nickel was added to the resulting residue. The mixture was stirred in a hydrogen atmosphere for 6 hours, N,N-dimethylformamide was added and the insoluble matters were filtered off. The solvent was evaporated in vacuo and water was added to the resulting residue. The resulting precipitate was filtered and dried in vacuo to give 4.58 g of 2-amino-N-(5-chloro-2-pyridyl)-3-hydroxybenzamide.

Referential Example 17

2-Amino-N-(5-chloro-2-pyridyl)-3-hydroxybenzamide (3.06 g) and 1.80 g of N-chlorosucciimide were dissolved in 60 ml of N,N-dimethylformamide, the solution was stirred at 50° C. for 8 hours and at room temperature for 4 hours and the insoluble matters were filtered off. After the solvent was evaporated in vacuo, a 1N aqueous solution of sodium hydroxide was added to the resulting residue, followed by extraction with ethyl acetate. The organic layer was dried over anhydrous magnesium sulfate, the solvent was evaporated in vacuo and the resulting residue was purified by silica gel column chromatography. Ethanol was added to the resulting crudely purified product and the resulting precipitate was filtered and dried in vacuo to give 767 mg of 2-amino-5-chloro-N-(5-chloro-2-pyridyl)-3-hydroxybenzamide. The mother liquor was concentrated, a mixture of ethyl acetate and isopropyl ether was added and the resulting precipitate was filtered and dried in vacuo to give additional 942 mg of the above compound.

Compounds of Referential Examples 18 and 19 were synthesized in the same manner as in Referential Example 17.

Referential Example 20

Ethyl 2-amino-5-chloro-3-hydroxybenzoate (3.23 g) was dissolved in 160 ml of a 3N aqueous solution of hydrochloric acid and stirred at 85° C. for 3 hours and at 80° C. for 5 days. The reaction solution was cooled to room temperature, insoluble matters were filtered off, 320 ml of a 1N aqueous solution of sodium hydroxide was added to the filtrate and the mixture was stirred at room temperature for 1 hour. The resulting precipitate was filtered, washed with pure water and dried in vacuo to give 1.55 g of 2-amino-5-chloro-3-hydroxybenzoic acid.

Referential Example 21

2-Amino-5-chloro-3-hydroxybenzoic acid (1.12 g) was dissolved in 60 ml of N,N-dimethylformamide, then 7.38 g of 4-methoxyaniline, 1.73 g of 1-ethyl-3-dimethylaminopropylcarbodiimide hydrochloride, 1.21 g of 1-hydroxybenzotriazole and 1.26 ml of triethylamine were added thereto and the mixture was stirred at room temperature for 13 hours. The reaction solution was concentrated in vacuo, ethyl acetate was added to the resulting residue and the mixture was washed with pure water and a saturated aqueous solution of sodium chloride, dried over magnesium sulfate and concentrated in vacuo. Chloroform was added to the resulting residue, the mixture was stirred for 30 minutes and the resulting precipitate was filtered, washed with chloroform and dried in vacuo to give 0.96 g of 2-amino-5-chloro-3-hydroxy-4'-methoxy-2-benzanilide.

Referential Example 22

Thionyl chloride (40 ml) was added to 5.09 g of 4-(4-methyl-1,4-diazepan-1-yl)benzoic acid hydrochloride and the mixture was stirred at 60° C. for 30 minutes. The reaction solution was concentrated to dryness in vacuo. To the resulting residue, a solution of 5.65 g of ethyl 3-amino-4-[(3-cyanophenylamino)methyl]benzoate in 50 ml of pyridine was added, and the mixture was stirred at room temperature for 5 hours. The reaction solution was concentrated in vacuo, and ethyl acetate and chloroform were added to the resulting residue. The mixture was washed with a saturated aqueous solution of sodium bicarbonate and a saturated aqueous solution of sodium chloride, dried over anhydrous magnesium sulfate and concentrated in vacuo. The resulting residue was purified by silica gel column chromatography using hexane-ethyl acetate (95:5 to 90:10) as an eluting solvent to give 6.42 g of ethyl 4-[(3-cyanophenylamino)methyl]-3-[4-(4-methyl-1,4-diazepan-1-yl)benzoylamino]benzoate.

A compound of Referential Example 23 was synthesized in the same manner as in Referential Example 22.

EXAMPLE 1

Ethyl 4-[(3-cyanophenylamino)methyl]-3-[4-(4-methyl-1,4-diazepan-1-yl)benzoylamino]benzoate (4.09 g) was dissolved in 80 ml of ethanol and hydrogen chloride gas was passed therethrough at −20° C. or lower for 20 minutes. The temperature was increased to 3° C. and the mixture was stirred for 24 hours. The reaction solution was concentrated to dryness in vacuo. The resulting residue was dissolved in 80 ml of ethanol, then 6.16 g of ammonium acetate was added and the mixture was stirred at room temperature for 3.5 days. The reaction solution was concentrated in vacuo, and the resulting residue was purified by ODS column chromatography using 0.002N aqueous solution of hydrochloric acid-ethanol (100:0 to 80:20) as an eluting solvent to give 3.84 g of ethyl 4-[(3-carbamimidoylphenylamino)methyl]-3-[4-(4-methyl-1,4-diazepan-1-yl)benzoylamino]benzoate hydrochloride. The resulting compound (1.70 g) was dissolved in 20 ml of ethanol, then 30 ml of a 1N aqueous solution of sodium hydroxide was added and the mixture was stirred at room temperature for one hour. The reaction solution was neutralized with a 1N aqueous solution of hydrochloric acid and concentrated in vacuo. The resulting residue was purified by ODS column chromatography using 0.002N aqueous solution of hydrochloric acid-acetonitrile (100:0 to 92:8) as an eluting solvent and freeze-dried to give 1.48 g of 4-[(3-carbamimidoylphenylamino)methyl]-3-[4-(4-methyl-1,4-diazepan-1-yl)benzoylamino]benzoic acid hydrochloride.

EXAMPLE 2

Ethyl 4-[(3-cyanophenylamino)methyl]-3-[4-(4-methyl-1,4-diazepan-1-yl)benzoylamino]benzoate (1.42 g) was dissolved in 30 ml of ethanol, then 291 mg of hydroxylamine hydrochloride and 0.78 ml of triethylamine were added and the mixture was stirred at 60° C. for 24 hours. The reaction solution was concentrated in vacuo and the resulting residue was purified by silica gel column chromatography using chloroform-methanol-aqueous ammonia (100:0:0 to 92:8:0.8) to give a crudely purified product, ethyl 4-({[3-(N-hydroxycarbamimidoyl)phenyl]amino}methyl)-3-[4-(4-methyl-1,4-diazepan-1-yl)benzoylamino]benzoate. The crudely purified product was further purified by ODS column chromatography using 0.002N aqueous solution of hydrochloric acid-methanol (100:0 to 88:12) as an eluting solvent and freeze-dried to give 1.03 g of ethyl 4-({[3-(N-hydroxycarbamimidoyl)phenyl]amino}methyl)-3-[4-(4-methyl-1,4-diazepan-1-yl)benzoylamino]benzoate hydrochloride.

Compounds of Examples 3, 5, 7 and 54 were synthesized in the same manner as in Example 1.

Compounds of Examples 4, 6, 8 and 53 were synthesized in the same manner as in Example 2.

EXAMPLE 9

4-(4-Methyl-1,4-diazepan-1-yl)benzoic acid hydrochloride (812 mg) was dissolved in 8 ml of thionyl chloride and stirred at 60° C. for 30 minutes. The reaction solution was concentrated to dryness in vacuo. A solution where 774 mg of 2-amino-4'-methoxy-3-hydroxybenzanilide was dissolved in 15 ml of pyridine was added to the resulting residue at 0° C. and the mixture was stirred at room temperature for 2 hours. The reaction solution was concentrated in vacuo, toluene was added to the resulting residue and the mixture was concentrated in vacuo again. To the resulting residue were added a saturated aqueous solution of sodium bicarbonate and ethyl acetate and the resulting precipitate was filtered. The ethyl acetate layer of the mother liquor was dried over anhydrous sodium sulfate and concentrated in vacuo. The resulting residue was mixed with the filtered precipitate and purified by silica gel column chromatography using chloroform-methanol (98:2) as an eluting solvent to give 873 mg of 3-hydroxy-4'-methoxy-2-{[4-(4-methyl-1,4-diazepan-1-yl)benzoyl]amino}benzanilide. The resulting compound was suspended in 10 ml of ethanol, 0.7 ml of a 4N solution of hydrochloric acid in ethyl acetate was added, the mixture was stirred and the resulting precipitate was filtered, washed with ethanol and dried in vacuo to give 896 mg of 3-hydroxy-4'-methoxy-2-{[4-(4-methyl-1,4-diazapan-1-yl)benzoyl]amino}benzanilide hydrochloride.

Compounds of Examples 10 to 16, 42, 51 and 52 were synthesized in the same manner as in Example 9.

EXAMPLE 17

2'-Amino-6'-hydroxy-4-(4-methyl-1,4-diazapan-1-yl) benzanilide (2.03 g) was dissolved in 60 ml of pyridine, 1.12 g of 4-methoxybenzoyl chloride was added at 0° C. and the mixture was stirred at room temperature for 3 days. The reaction solution was concentrated in vacuo, then 150 ml of chloroform was added to the resulting residue and the mixture was made alkaline with 150 ml of a 5% aqueous solution of sodium bicarbonate and extracted with chloroform. The resulting organic layer was dried over anhydrous sodium sulfate and concentrated in vacuo, toluene was added thereto and the mixture was concentrated in vacuo again. The resulting residue was purified by silica gel column chromatography using chloroform-methanol-saturated aqueous ammonia (100:10:1) as an eluting solvent. This was recrystallized from ethanol to give 1.74 g of 3-hydroxy-$N^1$-(4-methoxybenzoyl)-$N^2$-[4-(4-methyl-1,4-diazepan-1-yl)benzoyl]-1,2-phenylenediamine. 3-Hydroxy-$N^1$-(4-methoxybenzoyl)-$N^2$-[4-(4-methyl-1,4-diazepan-1-yl)benzoyl]-1,2-phenylenediamine (1.10 g) and 269 mg of maleic acid were dissolved under heating in 11 ml of a 50% aqueous solution of methanol, and 11 ml of water was added for cooling. Crystals thus formed were collected by filtration and dried to give 1.18 g of 3-hydroxy-$N^1$-(4-methoxybenzoyl)-$N^2$-[4-(4-methyl-1,4-diazepan-1-yl) benzoyl]-1,2-phenylenediamine maleate.

Compounds of Examples 18 to 35 were synthesized in the same manner as in Example 17.

EXAMPLE 36

3-Hydroxy-$N^1$-(4-methoxybenzoyl)-$N^2$-[4-(4-methyl-1, 4-diazepan-1-yl)benzoyl]-1,2-phenylenediamine (500 mg)

was dissolved in 11 ml of methanol, then 215 mg of benzyl bromide was added at room temperature and the mixture was stirred for 5 hours. Benzyl bromide (215 g) was further added at room temperature and the mixture was stirred for 16 hours. The resulting deposit was collected by filtration and suspended in 11 ml of N,N-dimethylformamide, then 210 mg of ethyl bromoacetate and 174 mg of potassium carbonate were added and the mixture was stirred at 100° C. for 30 minutes. Insoluble matters were filtered off, followed by concentration in vacuo. The resulting residue was dissolved in 16 ml of acetic acid, then 100 mg of a 10% palladium-carbon powder was added and the mixture was stirred in a hydrogen atmosphere of 3 atm. at room temperature for 3 hours. The reaction solution was filtered through Celite and washed with methanol, and the filtrate was concentrated in vacuo. Chloroform (50 ml) was added to the resulting residue, and the mixture was made alkaline with 50 ml of a 5% aqueous solution of sodium bicarbonate, followed by extraction with chloroform. The resulting organic layer was dried over anhydrous sodium sulfate and concentrated in vacuo. The resulting residue was purified by silica gel column chromatography using chloroform-methanol-saturated aqueous ammonia (100:10:1) as an eluting solvent to give 580 mg of a crudely purified product, ethyl(3-[(4-methoxybenzoyl)amino]-2-{[4-(4-methyl-1,4-diazepan-1-yl)benzoyl]amino}phenoxy)acetate. The crudely purified product was purified by ODS column chromatography using 0.001N hydrochloric acid-methanol (10:4) as an eluting solvent to give 350 mg of ethyl(3-[(4-methoxybenzoyl)amino]-2-{[4-(4-methyl-1,4-diazepan-1-yl)benzoyl]amino}phenoxy)acetate hydrochloride.

EXAMPLE 37

Ethyl(3-[(4-methoxybenzoyl)amino]-2-{[4-(4-methyl-1,4-diazepan-1-yl)benzoyl]amino}phenoxy)acetate hydrochloride (350 mg) was dissolved in 6 ml of methanol, then 1.8 ml of a 1N aqueous solution of sodium hydroxide was added at room temperature and the mixture was stirred for 2 hours. 1N hydrochloric acid (1.8 ml) was further added and the mixture was concentrated in vacuo. The resulting residue was purified by ODS column chromatography using 0.001N hydrochloric acid-acetonitrile (1:1) as an eluting solvent to give 254 mg of (3-[(4-methoxybenzoyl)amino]-2-{[4-(4-methyl-1,4-diazepan-1-yl)benzoyl]amino}phenoxy)acetic acid hydrochloride.

A compound of Example 38 was synthesized in the same manner as in Example 37.

EXAMPLE 39

A crudely purified product (370 mg) of ethyl(3-[(4-methoxybenzoyl)amino]-2-{[4-(4-methyl-1,4-diazepan-1-yl)benzoyl]amino}phenoxy)acetate was dissolved in 7 ml of tetrahydrofuran and 108 mg of sodium tetrahydroborate was added at room temperature. A solution of 930 mg of methanol in 7 ml of tetrahydrofuran was added dropwise thereto at 60° C. over 25 minutes. The mixture was stirred at 60° C. for 2 hours. Water (1 ml) was further added at room temperature and the mixture was concentrated in vacuo. The resulting residue was again subjected to the above-described operation and the resulting residue was purified by silica gel column chromatography using chloroform-methanol-saturated aqueous ammonia (100:10:1) as an eluting solvent. The resulting compound was suspended in 3 ml of ethanol, then 0.4 ml of 1N hydrochloric acid was added and the mixture was concentrated in vacuo. Acetone (3 ml) and 3 ml of distilled water were added to the resulting residue, and a precipitate thus formed was filtered to give 107 mg of 3-(2-hydroxyethoxy)-$N^1$-(4-methoxybenzoyl)-$N^2$-[4-(4-methyl-1,4-diazepan-1-yl)benzoyl]-1,2-phenylenediamine hydrochloride.

EXAMPLE 40

3-Hydroxy-$N^1$-(4-methoxybenzoyl)-$N^2$-[4-(4-methyl-1,4-diazepan-1-yl)benzoyl]-1,2-phenylenediamine (730 mg) was dissolved in 20 ml of tetrahydrofuran, then 0.13 ml of methanol, 498 mg of triphenylphosphine and 0.23 ml of diethyl azodicarboxylate were added and the mixture was stirred at room temperature for 16.5 hours. The reaction solution was concentrated in vacuo and the resulting residue was dissolved in chloroform. The solution was washed with a 0.5N aqueous solution of sodium hydroxide and a saturated aqueous solution of sodium chloride and dried over anhydrous sodium sulfate, followed by concentration in vacuo. The resulting residue was purified by silica gel column chromatography using chloroform-methanol (95:5 to 93:7) as an eluting solvent. The resulting crudely purified product was dissolved in 10 ml of ethanol, then 0.4 ml of a 4N hydrochloric acid-ethyl acetate solution was added and the mixture was concentrated in vacuo. The resulting residue was purified by ODS column chromatography using 0.002N aqueous solution of hydrochloric acid-acetonitrile (97:3 to 85:15) as an eluting solvent and freeze-dried to give 335 mg of 3-methoxy-$N^1$-(4-methoxybenzoyl)-$N^2$-[4-(4-methyl-1,4-diazepan-1-yl)benzoyl]-1,2-phenylenediamine hydrochloride.

EXAMPLE 41

3-Hydroxy-$N^1$-(4-methoxybenzoyl)-$N^2$-[4-(4-methyl-1,4-diazepan-1-yl)benzoyl]-1,2-phenylenediamine (474 mg) was dissolved in 15 ml of N,N-dimethylformamide, then 1.39 g of a trimethylamine-sulfur trioxide complex was added and the mixture was stirred at 60° C. for 79 hours. Further, 0.42 g of a trimethylamine-sulfur trioxide complex was added and the mixture was stirred at 60° C. for 38 hours. Still further, 0.42 g of a trimethylamine-sulfur trioxide complex was added and the mixture was stirred at 60° C. for 23 hours and concentrated in vacuo. Water was added to the resulting residue and the mixture was stirred for one hour. A precipitate thus formed was collected by filtration and washed with water. The resulting crudely purified product was suspended in ethanol and the suspension was stirred and filtered. The resulting residue was washed with ethanol and water and dried in vacuo to give 483 mg of 3-[(4-methoxybenzoyl)amino]-2-{[4-(4-methyl-1,4-diazepan-1-yl)benzoyl]amino}phenyl hydrogen sulfate.

EXAMPLE 43

$N^2$-[4-(4-Benzyl-1,4-diazepan-1-yl)benzoyl]-3-hydroxy-$N^1$-(4-methoxybenzoyl)-1,2-phenylenediamine (11.53 g) was dissolved in 250 ml of acetic acid, then 2.5 g of a 10% palladium-carbon powder was added and the mixture was stirred in a hydrogen atmosphere of 3 atm. at room temperature for 44 hours. The reaction solution was filtered through Celite and washed with acetic acid, and the filtrate was concentrated in vacuo. Toluene was added and the mixture was again concentrated in vacuo to give 11.11 g of a residue. The residue (2.00 g) was dissolved in a mixed solvent of chloroform, an aqueous solution of sodium bicarbonate and methanol and the mixture was stirred for 12 hours. The organic layer was separated, washed with a saturated aqueous solution of sodium chloride, dried over anhydrous magnesium sulfate and concentrated in vacuo.

The resulting residue was suspended in ethanol and the suspension was stirred for 3 hours. A precipitate thus formed was filtered and washed with ethanol. The resulting solid was recrystallized from ethanol to give $N^2$-[4-(1,4-diazepan-1-yl)benzoyl]-3-hydroxy-$N^1$-(4-methoxybenzoyl)-1,2-phenylenediamine. This product was further crystallized from 0.5N HCl to give 878 mg of $N^2$-[4-(1,4-diazepan-1-yl)benzoyl]-3-hydroxy-$N^1$-(4-methoxybenzoyl)-1,2-phenylenediamine hydrochloride.

EXAMPLE 44

3-Hydroxy-$N^1$-(4-methoxybenzoyl)-$N^2$-[4-(1,4-diazepan-1-yl)benzoyl]-1,2-phenylenediamine (857 mg) was suspended in 20 ml of dichloroethane, and 1.2 g of acetic acid, 261 mg of cyclopropanecarbaldehyde and 789 mg of triacetoxyborohydride were added at room temperature. The mixture was stirred for 2 hours, then 261 mg of cyclopropanecarbaldehyde and 789 mg of triacetoxyborohydride were added at room temperature, and the mixture was further stirred for 2 hours. The reaction solution was concentrated in vacuo and 50 ml of chloroform was added to the resulting residue. The mixture was made alkaline with 50 ml of a 5% aqueous solution of sodium bicarbonate and extracted with chloroform. The resulting organic layer was dried over anhydrous sodium sulfate and concentrated in vacuo. The resulting residue was purified by silica gel column chromatography using chloroform-methanol-saturated aqueous ammonia (100:10:1) as an eluting solvent. The resulting compound was suspended in 13 ml of ethanol and 1.9 ml of 1N hydrochloric acid was added. A precipitate thus formed was filtered to give 656 mg of 3-hydroxy-$N^1$-(4-methoxybenzoyl)-$N^2$-[4-(4-cyclopropylmethyl-1,4-diazepan-1-yl)benzoyl]-1,2-phenylenediamine hydrochloride.

EXAMPLE 45

$N^2$-[4-(1,4-Diazepan-1-yl)benzoyl]-3-hydroxy-$N^1$-(4-methoxybenzoyl)-1,2-phenylenediamine (1.3 g) was dissolved in 20 ml of ethanol, then 1.04 g of ethyl acetoimidate hydrochloride and 1.5 ml of triethylamine were added, and the mixture was stirred for 17 hours. Ethanol (150 ml), 1.04 g of ethyl acetoimidate hydrochloride and 1.5 ml of triethylamine were further added, and the mixture was stirred at 50° C. for 68 hours. The reaction solution was concentrated in vacuo. The resulting residue was purified by ODS column chromatography using 0.002 N aqueous solution of hydrochloric acid-acetonitrile (95:5 to 70:30) as an eluting solvent and freeze-dried to give 515 mg of 3-hydroxy-$N^2$-{4-[4-(1-iminoethyl)-1,4-diazepan-1-yl]benzoyl}-$N^1$-(4-methoxybenzoyl)-1,2-phenylenediamine hydrochloride.

Compounds of Examples 46 to 48 were synthesized in the same manner as in Example 44.

EXAMPLE 49

4-(4-Methyl-1,4-diazepan-1-yl)benzoic acid hydrochloride (755 mg) was dissolved in 2.2 ml of thionyl chloride and stirred at 60° C. for 30 minutes. The reaction solution was concentrated and dried in vacuo. To the residue was added a solution of 891 mg of 2-amino-5-chloro-N-(5-chloro-2-pyridyl)-3-hydroxybenzamide in 10 ml of pyridine and the mixture was stirred at room temperature for 13 hours. The reaction solution was concentrated in vacuo, 20 ml of acetic acid was added to the resulting residue and the mixture was stirred at room temperature for 17 hours. The reaction solution was concentrated in vacuo, a saturated aqueous solution of sodium bicarbonate was added to the resulting residue and the mixture was extracted with chloroform, dried over anhydrous sodium sulfate and concentrated in vacuo. The residue was purified by silica gel column chromatography using chloroform-methanol-aqueous ammonia (97:3:0.3 to 95:5:0.5) as an eluting solvent to give a crudely purified product, 5-chloro-N-(5-chloro-2-pyridyl)-3-hydroxy-2-{[4-(4-methyl-1,4-diazapan-1-yl)benzoyl]amino}benzamide. This was further purified by ODS column chromatography using acetonitrile-0.002N aqueous solution of hydrochloric acid (2:8 to 3:7) as an eluting solvent, suspended in a diluted aqueous solution of hydrochloric acid and freeze-dried to give 492 mg of 5-chloro-N-(5-chloro-2-pyridyl)-3-hydroxy-2-{[4-(4-methyl-1,4-diazapan-1-yl)benzoyl]amino}benzamide hydrochloride.

A compound of Example 50 was synthesized in the same manner as in Example 49.

Structural formulae and physicochemical properties of the compounds of the above Referential Examples and Examples are shown in Tables 2 and 3. The compounds shown in Tables 4 to 6 can be easily produced in manners substantially the same as those described in the Examples or Production Methods, or by applying thereto slightly modified methods that are obvious to those skilled in the art. The symbols in the tables have the following meanings.

Rf: Referential Example No.

Ex: Example No.

structure: Structural formula salt: Salt free: Free substance

DATA: Physical properties data

NMR: Nucleomagnetic resonance spectrum (TMS internal standard)

FAB-MS: Mass analytical value

Me: Methyl

Et: Ethyl

TABLE 2

| Rf | structure (salt) | DATA |
|---|---|---|
| 1 | (structure: NC-phenyl-NH-CH2-phenyl(NO2)(COOEt)) (free) | NMR(CDCl$_3$): δ: 1.42(3H, t, J=7.2Hz), 4.43(2H, q, J=7.2Hz), 4.63(1H, t, J=5.7Hz), 4.81(2H, d, J=6.0Hz), 6.72–6.78(2H, m), 7.01(1H, dt, J=1.3Hz, 7.7Hz), 7.19–7.27(1H, m), 7.69(1H, d, J=8.1Hz), 8.24(1H, dd, J=1.7Hz, 8.0Hz), 8.73(1H, d, J=1.7Hz) |

TABLE 2-continued

| Rf | structure (salt) | DATA |
|---|---|---|
| 2 | 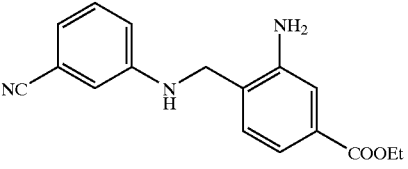 (free) | NMR(CDCl₃): δ: 1.39(3H, t, J=7.1Hz), 3.96–4.16(3H, m), 4.25(2H, d, J=4.2Hz), 4.36(2H, q, J=7.1Hz), 6.85–6.93(2H, m), 7.05(1H, dt, J=1.2Hz, 7.9Hz), 7.22(1H, d, J=7.7Hz), 7.27(1H, t, J=8.0Hz), 7.41(1H, d, J=Hz), 7.43(1H, dd, J=1.7Hz, 7.7Hz) |
| 3 | 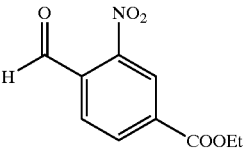 (free) | NMR(CDCl₃): δ: 1.46(3H, t, J=7.2Hz), 4.48(2H, q, J=7.2Hz), 8.00(1H, d, J=8.0Hz), 8.42(1H, d, J=8.0Hz), 8.75(1H, s), 10.46(1H, s) |
| 4 | 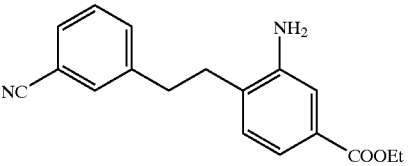 (free) | NMR(CDCl₃): δ: 1.38(3H, t, J=7.1Hz), 2.82(2H, t, J=8.4Hz), 2.96(2H, t, J=8.4Hz), 4.34(2H, q, J=7.1Hz), 6.97(1H, d, J=8.4Hz), 7.33–7.41(4H, m), 7.44–7.52(2H, m) |
| 5 | 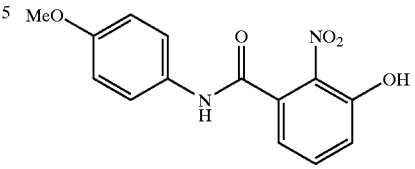 (free) | NMR(DMSO-d₆): δ: 3.74(3H, s), 6.92(2H, d, J=8.8Hz), 7.19–7.30(2H, m), 7.50(1H, t, J=8.6Hz), 7.58(2H, d, J=9.3Hz), 10.46(1H, s), 11.25 (1H, brs), |
| 6 | 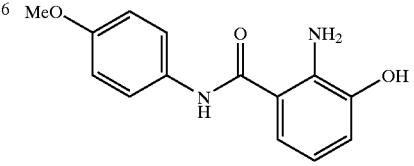 (free) | NMR(DMSO-d₆): δ: 3.74(3H, s), 5.79(2H, s), 6.46(1H, t, J=7.8Hz), 6.82(1H, d, J=7.8Hz), 6.90(2H, d, J=8.8Hz), 7.15(1H, d, J=7.8Hz), 7.61(2H, d, J=8.8Hz), 9.56(1H, s), 9.81(1H, s), |
| 7 | 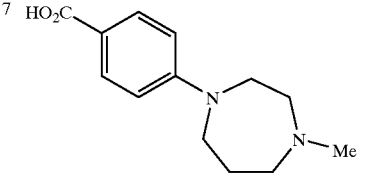 HCl | NMR(DMSO-d₆): δ: 2.06–2.24(1H, m), 2.30–2.45(1H, m), 2.77(3H, s), 3.00–3.24(2H, m), 3.24–3.55(4H, m), 3.70–4.00(2H, m), 6.81(2H, d, J=9.1Hz), 7.78(2H, d, J=9.1Hz), 11.06(1H, s), 12.20(1H, s) |

TABLE 2-continued

| Rf | structure (salt) | DATA |
|---|---|---|
| 8 | 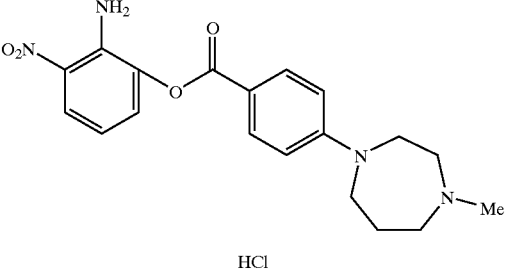<br>HCl | NMR(DMSO-d$_6$): δ: 2.15–2.22(1H, m), 2.34–2.45(1H, m), 2.79(3H, d, J=5.0Hz), 3.05–3.22(2H, m), 3.40–3.61(4H, m), 3.79–3.88(1H, m), 3.95–4.03(1H, m), 6.69–6.75(1H, m), 6.93(2H, d, J=9.0Hz), 7.05(2H, br), 8.00(2H, d, J=9.0Hz), 11.12(1H, br) |
| 9 | 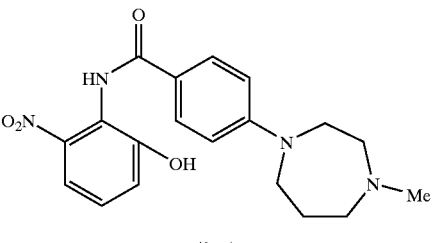<br>(free) | NMR(DMSO-d$_6$): δ: 1.86–1.95(2H, m), 2.29(3H, s), 2.45–2.52(2H, m), 2.65(2H, t, J=4.4Hz), 3.51(2H, t, J=6.0Hz), 3.60(2H, t, J=4.4Hz), 6.76(2H, d, J=9.2Hz), 7.21–7.28(2H, m), 7.35(1H, dd, J=6.8Hz, 2.4Hz), 7.84(2H, d, J=9.2Hz), 9.53(1H, br) |
| 10 | 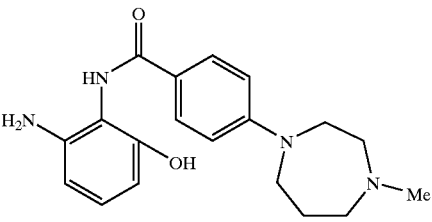<br>(free) | NMR(DMSO-d$_6$): 1.85–1.94(2H, m), 2.26(3H, s), 2.43(2H, t, J=5.6Hz), 2.61(2H, t, J=4.8Hz), 3.51(2H, t, J=6.0Hz), 3.58(2H, t, J=4.8Hz), 4.68(2H, s), 6.16(1H, dd, J=7.6Hz, 1.2Hz), 6.24(1H, dd, J=8.0Hz, 1.2Hz), 6.70–6.81(3H, m), 7.86(1H, d, J=8.8Hz), 8.93(1H, br), 8.94(1H, s) |
| 11 | 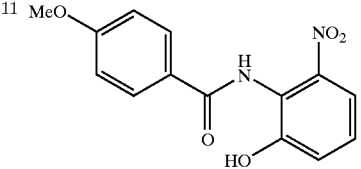<br>(free) | NMR(DMSO-d$_6$): δ: 3.88(3H, s), 6.70(1H, dd, J=7.7Hz, 8.7Hz), 7.14(2H, d, J=8.9Hz), 7.17–7.21(2H, m), 7.43(1H, dd, J=1.4Hz, 7.7Hz), 7.97(1H, dd, J=1.4Hz, 8.7Hz), 8.13(2H, d, J=8.9Hz) |
| 12 | 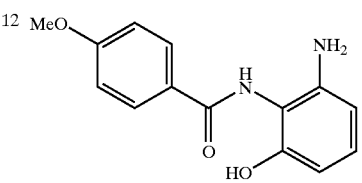<br>(free) | NMR(DMSO-d$_6$): δ: 3.83–3.86(2H, m), 3.84(3H, s), 6.68–6.72(1H, m), 6.72–6.78(1H, m), 7.06(2H, d, J=8.7Hz), 7.06–7.12(2H, m), 8.05(2H, d, J=8.7Hz), 9.63–9.67(1H, br) |
| 13 | 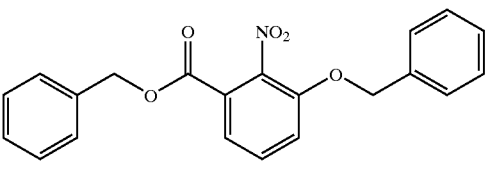<br>(free) | NMR(DMSO-d$_6$): δ: 5.33(4H, s), 7.31–7.45(10H, m), 7.61(1H, dd, J=1.4Hz, 7.5Hz), 7.68(1H, t, J=7.9Hz), 7.74(1H, dd, J=1.5Hz, 8.2Hz) |

TABLE 2-continued

| Rf | structure (salt) | DATA |
|---|---|---|
| 14 | 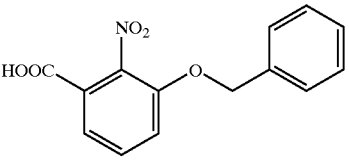 (free) | NMR(DMSO-d$_6$): δ: 5.32(2H, s), 7.31–7.44(5H, m), 7.56(1H, dd, J=1.7Hz, 7.3Hz), 7.64(1H, t, J=7.9Hz), 7.68(1H, dd, J=1.7Hz, 8.3Hz) |
| 15 | 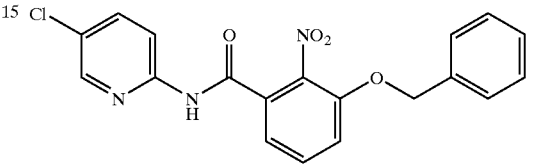 (free) | NMR(CDCl$_3$): δ: 5.23(2H, s), 7.22–7.26(2H, m), 7.31–7.39(5H, m), 7.46(1H, t, J=8.3Hz), 7.69(1H, dd, J=2.7Hz, 9.1Hz), 8.03(1H, d, J=2.9Hz), 8.26(1H, d, J=8.8Hz), 9.01(1H, brs) |
| 16 | 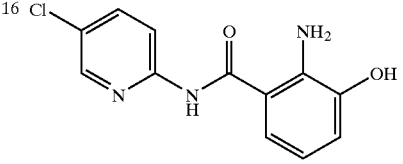 (free) | NMR(DMSO-d$_6$): δ: 5.93(2H, s), 6.44(1H, t, J=7.9Hz), 6.82(1H, d, J=7.7Hz), 7.27(1H, d, J=7.3Hz), 7.93(1H, dd, J=2.6Hz, 9.0Hz), 8.14(1H, d, J=8.8Hz), 8.41(1H, d, J=2.4Hz), 9.60(1H, s), 10.46(1H, s) |
| 17 | 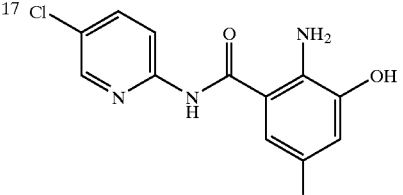 (free) | NMR(DMSO-d$_6$): δ: 6.04(2H, brs), 6.80(1H, d, J=2.4Hz), 7.36(1H, d, J=2.0Hz), 7.93(1H, dd, J=2.5Hz, 8.8Hz), 8.11(1H, d, J=9.3Hz), 8.42(1H, d, J=2.5Hz), 10.16(1H, brs), 10.67(1H, s) |
| 18 | 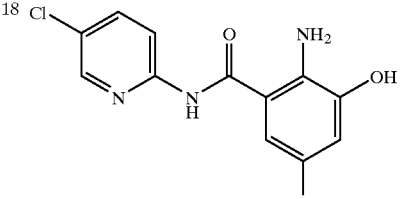 (free) | NMR(DMSO-d$_6$): δ: 6.06(2H, brs), 6.90(1H, d, J=2.2Hz), 7.47(1H, d, J=2.2Hz), 7.93(1H, dd, J=2.8Hz, 9.0Hz), 8.10(1H, d, J=9.0Hz), 8.42(1H, d, J=2.2Hz), 10.15(1H, brs), 10.69(1H, s) |
| 19 | 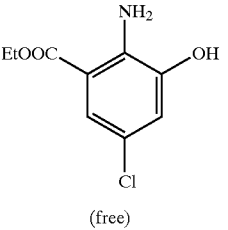 (free) | NMR(CDCl$_3$):δ: 1.38(3H, t, J=7.3Hz), 4.33(2H, q, J=7.3Hz), 5.00–6.30(3H br), 6.81(1H, d, J=2.0Hz), 7.48(1H, d, J=2.4Hz) |

TABLE 2-continued

| Rf | structure (salt) | DATA |
|---|---|---|
| 20 | 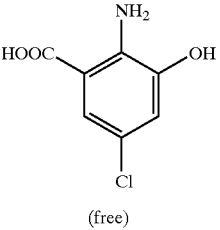<br>(free) | NMR(DMSO-d₆): δ: 3.37(1.5H, brs), 6.78(1H, d, J=2.4Hz), 7.17(1H, d, J=2.5Hz), 8.34(1.5H, brs), 10.19(1H, s) |
| 21 | 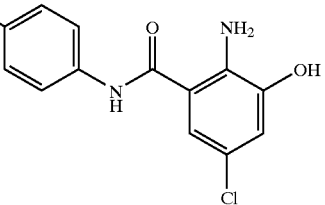<br>(free) | NMR(DMSO-d₆): δ: 3.74(3H, s), 5.93(2H, brs), 6.78(1H, d, J=1.9Hz), 6.91(2H, d, J=9.3Hz), 7.23(1H, d, J=2.5Hz), 7.59(2H, d, J=9.3Hz), 9.90(1H, s), 10.09(1H, brs) |
| 22 | 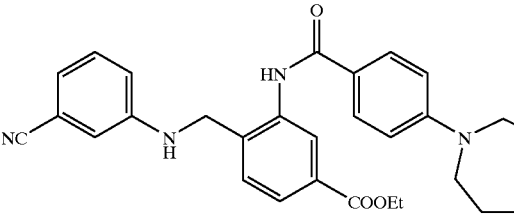<br>(free) | NMR(CDCl₃): δ: 1.39(3H, t, J=7.4Hz), 1.97–2.06(2H, m), 2.38(3H, s), 2.53–2.59(2H, m), 2.68–2.73(2H, m), 3.51(2H, t, J=6.4Hz), 3.57–3.63(2H, m), 4.34–4.42(5H, m), 6.58(2H, d, J=8.8Hz), 6.96–7.01(2H, m), 7.12(1H, d, J=7.8Hz), 7.31(1H, t, J=7.8Hz), 7.40(1H, d, J=8.3Hz), 7.65(2H, d, J=8.7Hz), 7.81(1H, dd, J=1.5Hz, 7.8Hz), 8.67(1H, d, J=2.0Hz), 8.85(1H, s), FAB-MS (m/z): 512 (M + H)⁺ |
| 23 | 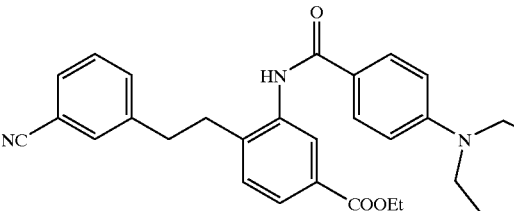<br>(free) | NMR(CDCl₃): δ: 1.37(3H, t, J=7.1Hz), 2.43–2.54(2H, br), 2.76(3H, s), 2.93–3.01(4H, m), 3.14–3.22(2H, br), 3.23–3.29(2H, br), 3.59(2H, t, J=6.4Hz), 3.89–3.95(2H, m), 4.33(2H, q, J=7.1Hz), 6.72(2H, d, J=8.9Hz), 7.20(1H, d, J=7.3Hz), 7.27–7.35(3H, m), 7.41(1H, d, J=7.3Hz), 7.68–7.73(1H, m), 7.75(2H, d, J=8.3Hz), 7.85(1H, dd, J=1.8Hz, 8.3Hz), 8.23 (1H, s) FAB-MS (m/z): 511 (M + H)⁺ |

TABLE 3

| Ex | structure (salt) | DATA |
|---|---|---|
| 1 | 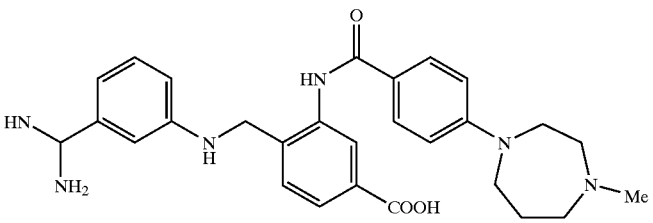<br>HCl | NMR(DMSO-d₆): δ: 2.16–2.26(2H, br), 2.67(3H, s), 2.95–3.49(5H, br), 3.54(2H, t, J=6.3Hz), 3.73–3.86(2H, br), 4.44(2H, d, J=5.3Hz), 6.79–6.87(4H, m), 6.94(1H, d, J=7.3Hz), 6.98(1H, s), 7.26(1H, t, J=8.3Hz), 7.44(1H, d, J=7.8Hz), 7.75(1H, dd, J=2.0Hz, 7.8Hz), 7.94(2H, d, J=9.2Hz), 7.98(1H, d, J=1.9Hz), 9.07(2H, s), 9.22(2H, s), 9.98(2H, s) FAB-MS (m/z): 501 (M + H)⁺ |

TABLE 3-continued

| Ex | structure (salt) | DATA |
|---|---|---|
| 2 | 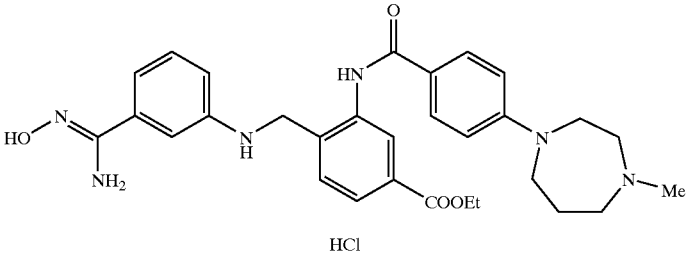 HCl | NMR(DMSO-$d_6$): δ: 1.31(3H, t, J=7.3Hz), 2.79(3H, d, J=4.4Hz), 4.31(2H, q, J=7.3Hz), 4.43(2H, s), 6.76–6.91(6H, m), 7.25(1H, t, J=8.4Hz), 7.46(1H, d, J=8.3Hz), 7.77(1H, dd, J=8.3, 1.4Hz), 7.96(2H, d, J=8.8Hz), 8.01(1H, d, J=1.4Hz), FAB-MS (m/z): 545 (M + H)$^+$ |
| 3 | 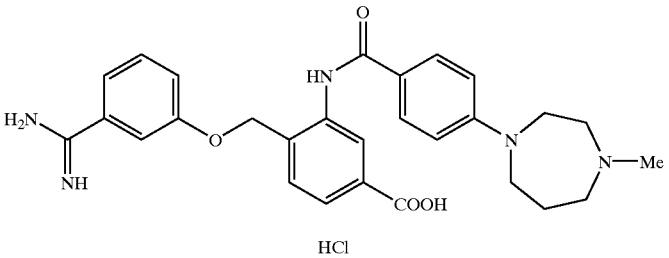 HCl | NMR(DMSO-$d_6$): δ: 2.02–2.09(2H, m), 2.76–2.84(2H, m), 2.87–2.98(2H, m), 3.32(3H, br s), 3.51–3.55(2H, m), 3.68–3.73(2H, m), 5.31(2H, s), 6.81(2H, d, J=8.8Hz), 7.31(1H, dd, J=2.4Hz, 8.4Hz), 7.40(1H, d, J=8.0Hz), 7.46–7.49(1H, m), 7.50–7.54(1H, m), 7.62(1H, d, J=8.4Hz), 7.82(1H, dd, J=2.0Hz, 8.0Hz), 7.89(2H, d, J=8.8Hz), 8.03(1H, d, J=1.6Hz), 9.33(4H, br s), 9.90(1H, s) FAB-MS (m/z): 502 (M + H)$^+$ |
| 4 | 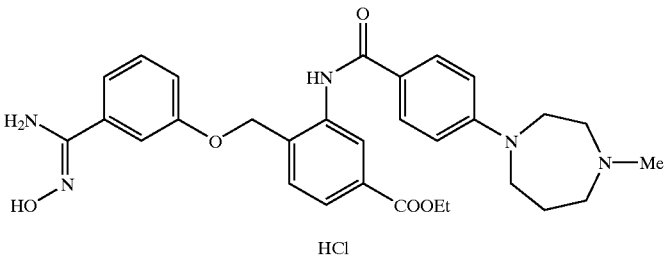 HCl | NMR(DMSO-$d_6$): δ: 1.33(3H, t, J=7.4Hz), 2.79(3H, s), 4.32(2H, q, J=7.3Hz), 5.26(2H, s), 6.86(2H, d, J=8.8Hz), 7.03–7.08(1H, m), 7.26–7.37(3H, m), 7.67(1H, d, J=8.4Hz), 7.84(1H, dd, J=1.6Hz, 8.4Hz), 7.91(2H, d, J=8.8Hz), 8.10(1H, d, J=1.6Hz), FAB-MS (m/z): 546 (M + H)$^+$ |
| 5 | 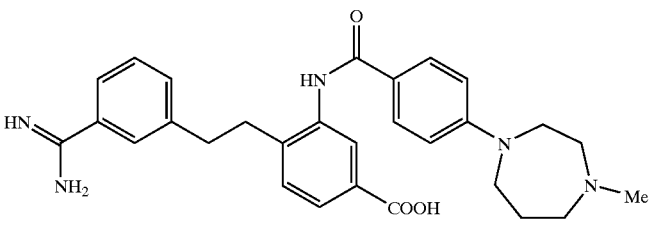 HCl | NMR(DMSO-$d_6$): δ: 2.12–2.24(1H, m), 2.38–2.49(1H, m), 2.79(3H, d, J=4.9Hz), 3.92–3.99(2H, m), 3.01–3.20(4H, m), 3.39–3.58(4H, m), 3.76–3.85(1H, m), 3.90–4.03(1H, m), 6.86(2H, d, J=9.3Hz), 7.41(1H, d, J=8.3Hz), 7.43–7.49(2H, m), 7.61–7.67(1H, m), 7.75(2H, dd, J=1.5Hz, 9.3Hz), 7.88(1H, d, J=1.5Hz), 7.98(2H, d, J=9.3Hz), 9.35(2H, s), 9.45(2H, s), 9.91(1H, s), 11.37(1H, s) FAB-MS (m/z): 500 (M + H)$^+$ |
| 6 | 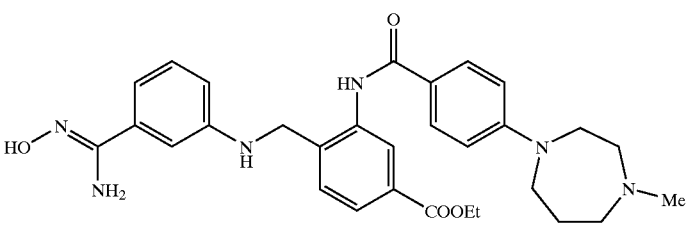 HCl | NMR(DMSO-$d_6$): δ: 1.32(3H, t, J=7.0Hz), 2.78(3H, s), 4.31(2H, q, J=7.0Hz), 6.86(2H, d, J=8.8Hz), 7.40–7.46(3H, m), 7.53(1H, dt, J=1.9Hz, 7.1Hz), 7.62(1H, s), 7.76(1H, dd, J=1.9Hz, 7.1Hz), 7.90(1H, d, J=1.4Hz), 7.96(2H, d, J=8.8Hz), FAB-MS (m/z): 544 (M + H)$^+$ |

TABLE 3-continued

| Ex | structure (salt) | DATA |
|---|---|---|
| 7 | 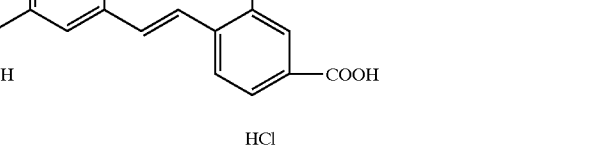 HCl | NMR(DMSO-d$_6$): δ: 2.79(3h, d, J=4.8Hz), 6.87(2H, d, J=8.8Hz), 7.43(1H, d, J=16.0Hz), 7.53(1H, d, J=16.0Hz), 7.60–7.64(1H, m), 7.73(1H, d, J=8.0Hz), 7.83(1H, dd, J=1.6Hz, 8.4Hz), 7.89(1H, d, J=7.6Hz), FAB-MS (m/z): 498 (M + H)$^+$ |
| 8 | 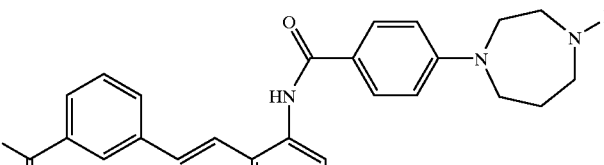 HCl | NMR(DMSO-d$_6$): δ: 1.33(3H, t, J=7.2Hz), 2.80(3H, d, J=4.8Hz), 4.34(2H, q, J=7.2Hz), 6.88(2H, d, J=9.2Hz), 7.42–7.51(2H, m), 7.58–7.65(2H, m), 7.84–7.87(2H, m), 7.90(1H, s), 7.96–8.01(4H, m) FAB-MS (m/z): 542 (M + H)$^+$ |
| 9 | 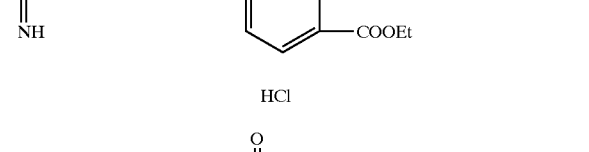 HCl | NMR(DMSO-d$_6$): δ: 2.10–2.41(2H, m), 2.78(3H, s), 3.02–3.22(2H, m), 3.35–3.57(4H, m), 3.67–3.81(4H, m), 3.87–3.99(1H, m), 6.80–6.95(4H, m), 7.11(1H, d, J=7.3Hz), 7.17–7.28(2H, m), 7.57(2H, d, J=8.8Hz), 7.85(2H, d, J=8.8Hz), 10.02(1H, s), 10.19(1H, s), 10.41(1H, s), 10.64(1H, brs) FAB-MS (m/z): 475 (M + H)$^+$ |
| 10 | 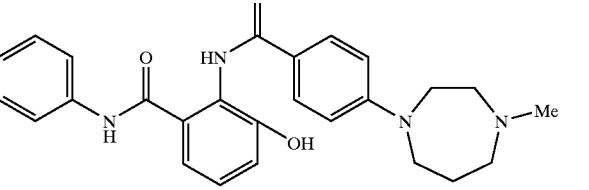 HCl | NMR(DMSO-d$_6$): δ: 2.78(3H, s), 6.84(2H, d, J=9.3Hz), 7.10–7.13(1H, m), 7.15–7.18(1H, m), 7.22–7.26(1H, m), 7.36(2H, d, J=8.8Hz), 7.71(2H, d, J=8.7Hz), 7.85(2H, d, J=8.8Hz) FAB-MS (m/z): 479 (M + H)$^+$ |
| 11 | 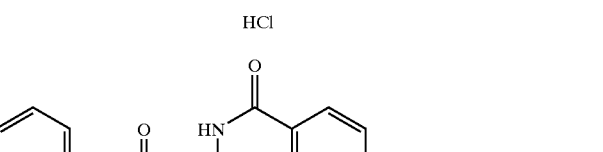 HCl | NMR(DMSO-d$_6$): δ: 2.10–2.22(1H, m), 2.28–2.41(1H, m), 2.77(3H, d, J=4.9Hz), 3.02–3.21(2H, m), 3.38–3.57(4H, m), 3.75(1H, dd, J=9.7Hz, 16.1Hz, 3.93(1H, dd, J=2.9Hz, 16.6Hz), 6.85(2H, d, J=8.8Hz), 7.09–7.27(5H, m), 7.69(2H, dd, J=5.1Hz, 9.1Hz), 7.85(2H, d, J=8.8Hz), 9.75–10.10(1H, br), 10.14(1H, s), 10.36(1H, s), 10.86(1H, brs) FAB-MS (m/z): 463 (M + H)$^+$ |
| 12 | 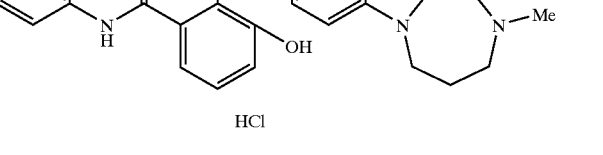 HCl | NMR(DMSO-d$_6$): δ: 2.11–2.40(2H, m), 2.27(3H, s), 2.78(3H, s), 3.01–3.22(2H, m), 3.38–3.55(4H, m), 3.73(1H, dd, J=9.7Hz, 16.1Hz), 3.93(1H, d, J=15.1Hz), 6.83–6.91(3H, m), 7.11(1H, dd, J=1.4Hz, 8.3Hz), 7.15–7.20(2H, m), 7.24(1H, d, J=7.8Hz), 7.44(1H, d, J=8.3Hz), 7.49(1H, s), 7.86(2H, d, J=8.8Hz), 9.96(1H, s), 10.14(1H, s), 10.17(1H, s), 10.54(1H, brs) FAB-MS (m/z): 459 (M + H)$^+$ |

TABLE 3-continued

| Ex | structure (salt) | DATA |
|---|---|---|
| 13 | 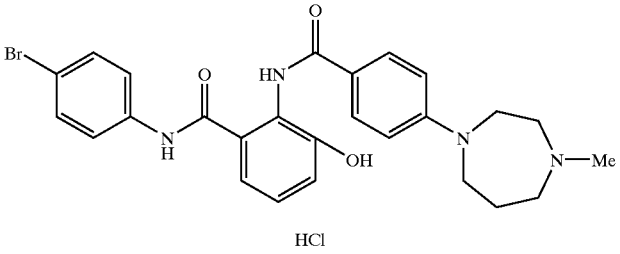 HCl | NMR(DMSO-d$_6$): δ: 2.79(3H, d, J=2.4Hz), 6.84(2H, d, J=9.3Hz), 7.11(1H, dd, J=1.3Hz, 8.1Hz), 7.16(1H, d, J=6.8Hz), 7.24(1H, t, J=7.8Hz), 7.48(2H, d, J=8.8Hz), 7.65(2H, d, J=8.8Hz), 7.84(2H, d, J=8.8Hz), 9.95(1H, s), 9.97(1H, s), 10.39(1H, s), 10.48–10.65(1H, br) FAB-MS (m/z): 523 (M + H)$^+$ |
| 14 | 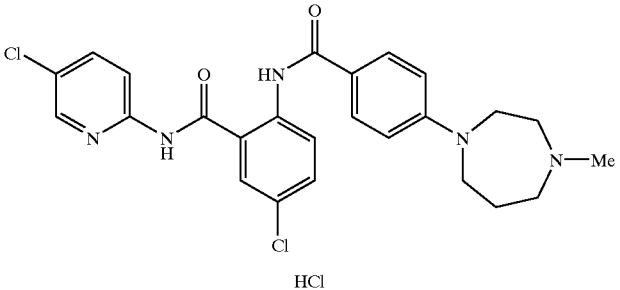 HCl | NMR(DMSO-d$_6$): δ: 2.12–2.20(1H, m), 2.32–2.43(1H, m), 2.78(3H, d, J=4.8Hz), 3.05–3.20(2H, m), 3.39–3.56(4H, m), 3.73–3.82(1H, m), 3.91–3.97(1H, m), 6.90(2H, d, J=8.7Hz), 7.65(1H, dd, J=2.4Hz, 8.8Hz), 7.79(2H, d, J=8.8Hz), 7.99–8.02(2H, m), 8.11(1H, d, J=8.8Hz), 8.43(1H, d, J=8.8Hz), 8.48(1H, d, J=2.5Hz), 10.94(1H, br s), 11.23(1H, s), 11.29(1H, s) FAB-MS (m/z): 498 (M)$^+$ |
| 15 | 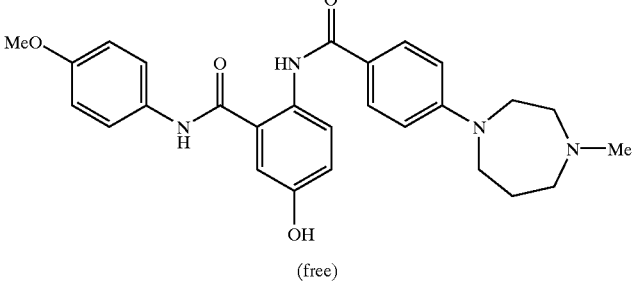 (free) | NMR(DMSO-d$_6$): δ: 2.25(3H, s), 3.75(3H, s), 6.79(2H, d, J=8.8Hz), 6.91–7.01(3H, m), 7.24(1H, d, J=2.5Hz), 7.61(2H, d, J=8.8Hz), 7.69(2H, d, J=8.8Hz), 8.28(1H, d, J=8.8Hz), FAB-MS (m/z): 475 (M + H)$^+$ |
| 16 | 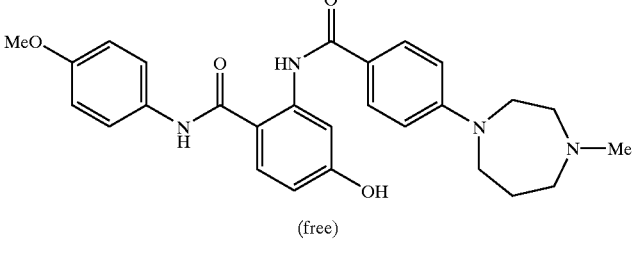 (free) | NMR(DMSO-d$_6$): δ: 2.25(3H, s), 3.76(3H, s), 6.55(1H, dd, J=8.8, 2.4Hz), 6.82(2H, d, J=9.3Hz), 6.95(2H, d, J=8.8Hz), 7.57(2H, d, J=8.8Hz), 7.74(2H, d, J=9.3Hz), 7.84(1H, d, J=8.8Hz), 8.27(1H, d, J=2.4Hz), FAB-MS (m/z): 475 (M + H)$^+$ |
| 17 | 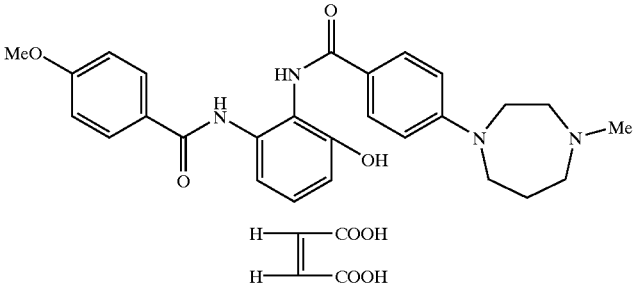 | NMR(DMSO-d$_6$): δ: 2.11–2.20(2H, m), 2.83(3H, s), 3.20–3.45(4H, m), 3.52(2H, t, J=6.0Hz), 3.72–3.88(5H, m), 6.03(2H, s), 6.80(1H, d, J=8.0Hz), 6.85(2H, d, J=8.8Hz), 7.04(2H, d, J=8.8Hz), 7.14(1H, t, J=8.0Hz), 7.24(1H, d, J=8.0Hz), 7.85(2H, d, J=8.8Hz), 7.91(2H, d, J=8.8Hz), 9.47(1H, s), 9.67(1H, s), 9.77(1H, s) FAB-MS (m/z): 475 (M + H)$^+$ |

TABLE 3-continued

| Ex | structure (salt) | DATA |
|---|---|---|
| 18 | 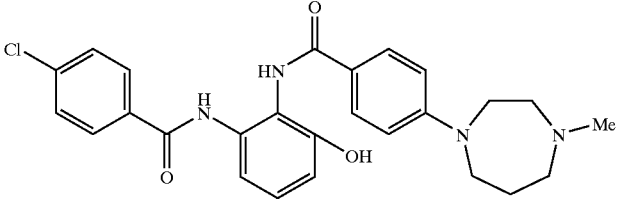 | NMR(DMSO-d$_6$): δ: 2.79(3H, s), 6.82–6.86(3H, m), 7.13–7.17(1H, m), 7.22(1H, d, J=8.3Hz), 7.58(2H, d, J=8.3Hz), 7.89–7.93(4H, m), FAB-MS (m/z): 479 (M + H)$^+$ |
| 19 | 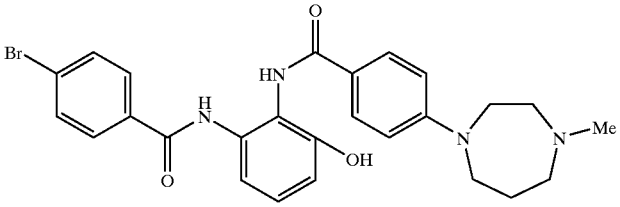 | NMR(DMSO-d$_6$): δ: 2.79(3H, s), 6.82–6.86(3H, m), 7.13–7.17(1H, m), 7.22(1H, d, J=7.8Hz), 7.72(2H, d, J=8.3Hz), 7.83(2H, d, J=8.3Hz), 7.92(2H, d, J=8.8Hz) FAB-MS (m/z): 523, 525 (M + H)$^+$ |
| 20 | 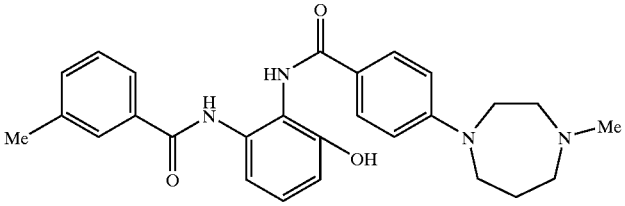 | NMR(DMSO-d$_6$): δ: 2.79(3H, s), 6.82(1H, d, J=8.3Hz), 6.86(2H, d, J=8.8Hz), 7.13–7.17(1H, m), 7.27(1H, d, J=8.4Hz), 7.36–7.79(2H, m), 7.64–7.68(2H, m), 7.95(2H, d, J=8.3Hz), 9.56(1H, s) FAB-MS (m/z): 459 (M + H)$^+$ |
| 21 | 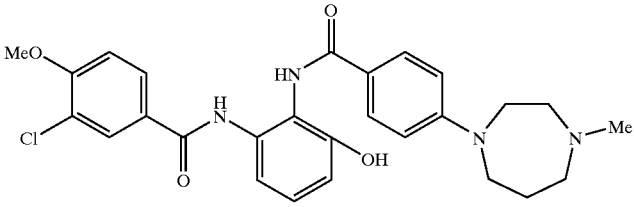 | NMR(DMSO-d$_6$): δ: 2.69(3H, s), 3.92(3H, s), 6.81–6.84(3H, m), 7.14(1H, dd, J=7.8, 8.3Hz), 7.22(1H, d, J=7.8Hz), 7.27(1H, d, J=8.8Hz), 7.88(1H, dd, J=2.0, 8.3Hz), 7.93(2H, d, J=8.8)), 7.95(1H, d, J=2.0Hz) FAB-MS m/z: 509 (M$^+$) |
| 22 | 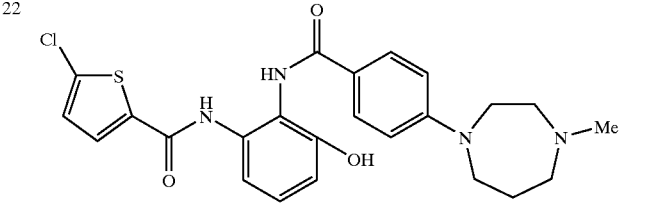 | NMR(DMSO-d$_6$): δ: 2.80(3H, d, J=3.9Hz), 6.79–6.88(3H, m), 7.10–7.18(2H, m), 7.24(1H, d, J=3.9Hz), 7.72(1H, d, J=3.9Hz), 7.95(2H, d, J=8.8Hz), FAB-MS m/z: 485 (M$^+$) |
| 23 | 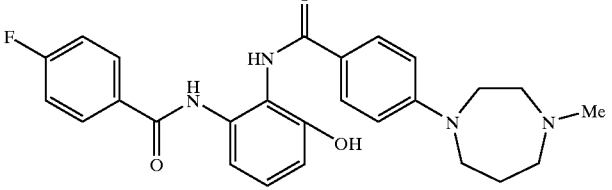 | NMR(DMSO-d$_6$): δ: 2.78(3H, s), 6.82–6.85(3H, m), 7.13–7.17(1H, m), 7.22(1H, d, J=7.8Hz), 7.32–7.37(2H, m), 7.93(2H, d, J=8.8Hz), 7.95–7.99(2H, m) FAB-MS (m/z): 463 (M + H)$^+$ |

TABLE 3-continued

| Ex | structure (salt) | DATA |
|---|---|---|
| 24 | 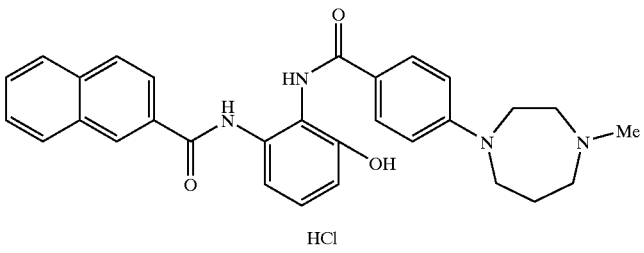 HCl | NMR(DMSO-d$_6$): δ: 2.76(3H, s), 6.83–6.87(3H, m), 7.16–7.20(1H, m), 7.31(1H, d, J=8.3Hz), 7.59–7.66(2H, m), 7.94–8.04(6H, m), 8.50(1H, s) FAB-MS (m/z): 495 (M + H)$^+$ |
| 25 | 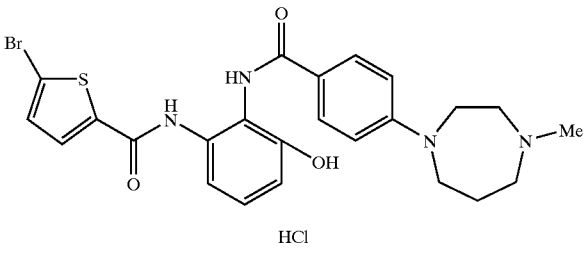 HCl | NMR(DMSO-d$_6$): δ: 2.80(3H, d, J=4.3Hz), 6.81–6.86(3H, m), 7.11–7.17(2H, m), 7.33(1H, d, J=3.9Hz), 7.66(1H, d, J=4.4Hz), 7.94(2H, d, J=8.8Hz) FAB (m/z): 529, 531 (M + H)$^+$ |
| 26 | 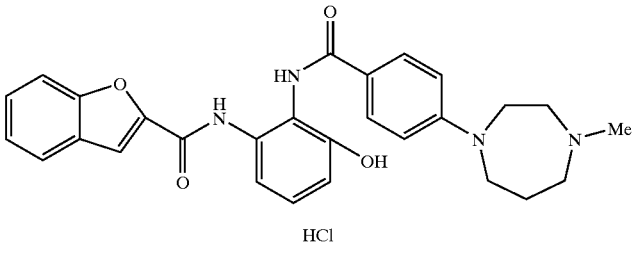 HCl | NMR(DMSO-d$_6$): δ: 2.75(3H, s), 6.84–6.88(3H, m), 7.15–7.19(1H, m), 7.33–7.37(2H, m), 7.47–7.51(1H, m), 7.57(1H, d, J=8.3Hz), 7.67(1H, s), 7.80(1H, d, J=7.8Hz), 8.00(2H, d, J=8.3Hz) FAB-MS (m/z): 485 (M + H)$^+$ |
| 27 | 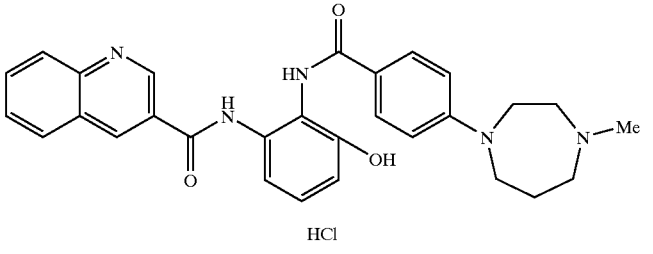 HCl | NMR(DMSO-d$_6$): δ: 2.75(3H, d, J=4.9Hz), 6.83(2H, d, J=9.3Hz), 6.88(1H, d, J=7.8Hz), 7.17–7.21(1H, m), 7.29(1H, d, J=7.8Hz), 7.79–7.82(1H, m), 7.98–8.01(3H, m), 8.17–8.20(2H, m), 9.16(1H, s), 9.44(1H, d, J=1.9Hz) FAB-MS(m/z): 496 (M + H)$^+$ |
| 28 | 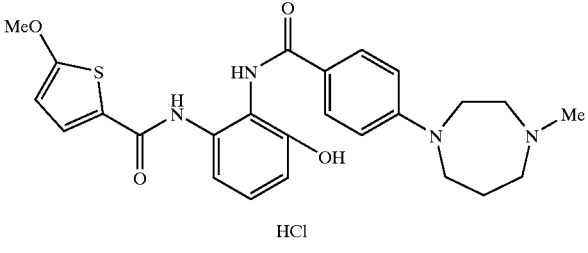 HCl | NMR(DMSO-d$_6$): δ: 2.80(3H, d, J=2.4Hz), 6.40(1H, d, J=3.9Hz), 6.80(1H, dd, J=1.5Hz, 7.8Hz), 6.86(2H, d, J=8.8Hz), 7.10–7.18(2H, m), 7.53(1H, d, J=3.9Hz), 7.94(2H, d, J=8.8Hz) FAB-MS (m/z): 481 (M + H)$^+$ |
| 29 | 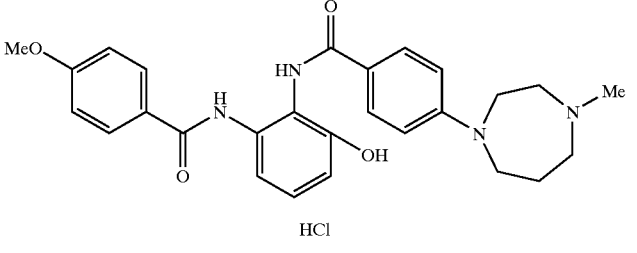 HCl | NMR(DMSO-d$_6$): δ: 2.79(3H, d, J=5.9Hz), 3.81(3H, s), 6.80(1H, d, J=8.3Hz), 6.85(1H, d, J=8.8Hz), 7.03(2H, d, J=8.8Hz), 7.12–7.17(1H, m), 7.24–7.27(1H, m), 7.86(2H, d, J=8.8Hz), 8.18(1H, d, J=8.7Hz), 8.79(1H, s) FAB-MS (m/z): 476 (M + H)$^+$ |

TABLE 3-continued

| Ex | structure (salt) | DATA |
|---|---|---|
| 30 | 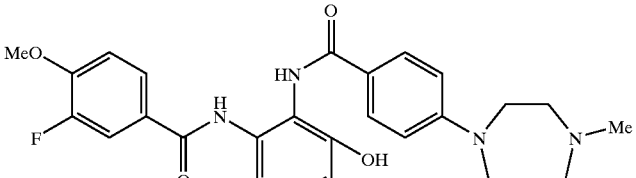 HCl | NMR(DMSO-d$_6$): δ: 2.79(3H, s), 6.82–6.86(3H, m), 7.12–7.16(1H, m), 7.22(1H, d, J=7.8Hz), 7.27–7.31(1H, m), 7.72–7.77(2H, m), 7.94(2H, d, J=8.3Hz), FAB-MS (m/z): 493 (M + H)$^+$ |
| 31 | 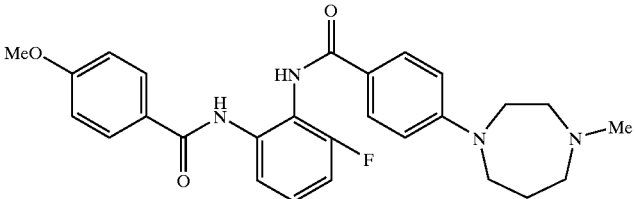 HCl | NMR(DMSO-d$_6$): δ: 2.79(3H, d, J=5.9Hz), 3.05–3.21(2H, m), 3.82(3H, s), 6.85(2H, d, J=9.3Hz), 7.03(2H, d, J=8.8Hz), 7.13–7.18(1H, m), 7.31–7.37(1H, m), 7.55–7.59(1H, m), 7.89(2H, d, J=8.8Hz), 7.94(2H, d, J=8.7Hz) FAB-MS (m/z): 477 (M + H)$^+$ |
| 32 | 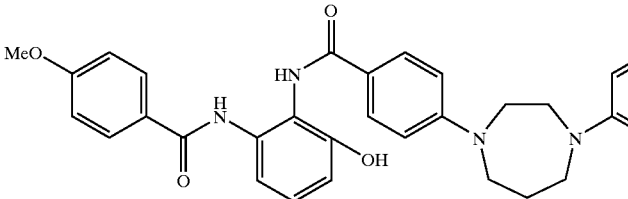 HCl | NMR(DMSO-d$_6$): δ: 1.82–2.01(2H, m), 3.46–3.89(11H, m), 6.80(1H, d, J=7.8Hz), 6.86(2H, d, J=8.8Hz), 6.97–7.21(5H, m), 7.25(1H, d, J=8.3Hz), 7.78–7.94(4H, m), 8.18(2H, s), 9.51(1H, s), 9.66(1H, brs), 9.82(1H, s), 13.46(1H, brs) FAB-MS (m/z): 5:38 (M + H)$^+$ |
| 33 | 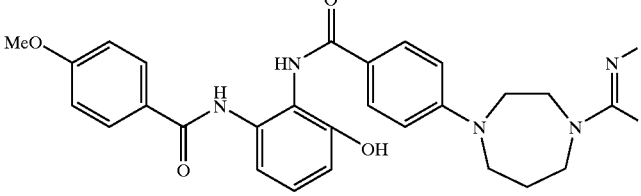 HCl | NMR(DMSO-d$_6$): δ: 2.24(1.5H, s), 2.26(1.5H, s), 2.84–2.95(3H, m), 6.81(1H, d, J=7.8Hz), 6.84–6.93(2H, m), 7.04(2H, d, J=8.8Hz), 7.14(1H, t, J=8.3Hz), 7.24(1H, d, J=8.3Hz), 7.87(2H, d, J=8.8Hz), 7.91(2H, d, J=8.9Hz) FAB-MS (m/z): 516 (M + H)$^+$ |
| 34 | 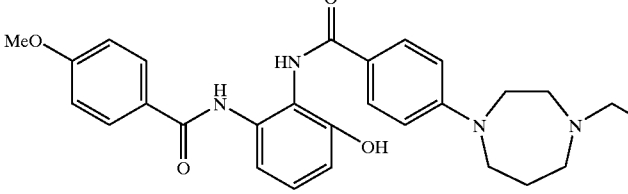 HCl | NMR(DMSO-d$_6$): δ: 6.80(1H, dd, J=0.9Hz, 8.3Hz), 6.85(2H, d, J=8 7Hz) 7.03(2H, d, J=8.7Hz), 7.14(1H, t, J=8.3Hz), 7.24(1H, d, J=7.8Hz), 7.43–7.51(3H, m), 7.54–7.61(2H, m), 7.86(2H, d, J=8.7Hz), 7.91(2H, d, J=8.7Hz) FAB-MS (m/z): 551 (M + H)$^+$ |
| 35 | 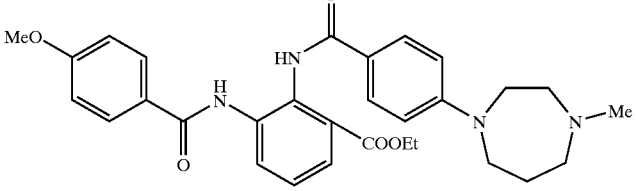 HCl | NMR(DMSO d$_6$): δ: 1.14(3H, t, J=6.8Hz), 2.80(3H, d, J=4.4Hz), 3.83(3H, s), 4.16(2H, q, J=7.2Hz), 6.86(2H, d, J=8.8Hz), 7.06(2H, d, J=8.8Hz), 7.39–7.43(1H, m), 7.68(1H, dd, J=1.5Hz, 7.8Hz), 7.86–7.88(3H, m), 7.94(2H, d, J=8.7Hz) FAB-MS (m/z): 531 (M + H)$^+$ |

TABLE 3-continued

| Ex | structure (salt) | DATA |
|---|---|---|
| 36 | 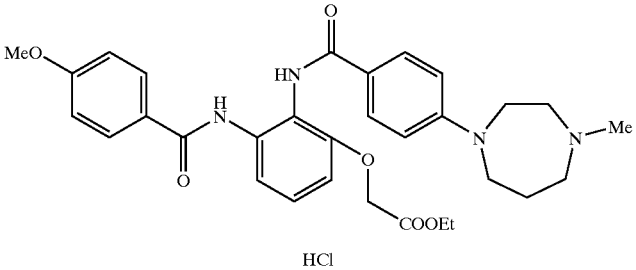 HCl | NMR(DMSO-d$_6$): δ: 1.21(3H, t, J=7.3Hz), 2.78(3H, d, J=4.9Hz), 4.17(2H, q, J=7.3Hz), 4.83(2H, s), 6.86(2H, d, J=9.3Hz), 6.92(1H, d, J=7.3Hz), 7.04(2H, d, J=8.8Hz), 7.25–7.29(1H, m), 7.49(1H, d, J=7.8Hz), 7.86(2H, d, J=8.8Hz), 7.93(2H, d, J=8.8Hz) FAB-MS (m/z): 561 (M + H)$^+$ |
| 37 | 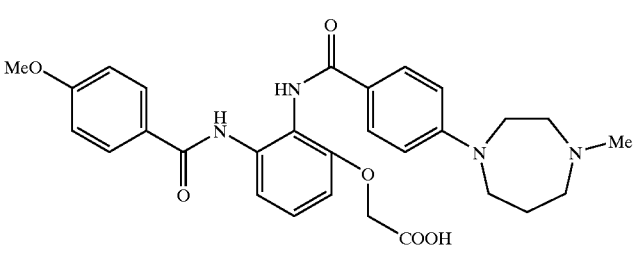 HCl | NMR(DMSO-d$_6$): δ: 2.78(3H, s), 4.75(2H, s), 6.86(2H, d, J=9.3Hz), 6.94(1H, d, J=7.3Hz), 7.04(2H, d, J=8.8Hz), 7.25–7.30(1H, m), 7.50(1H, d, J=7.9Hz), 7.85(2H, d, J=8.8Hz), 7.95(2H, d, J=8.8Hz) FAB-MS (m/z): 533 (M + H)$^+$ |
| 38 | 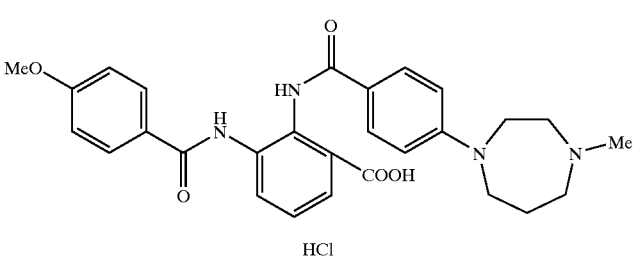 HCl | NMR(DMSO-d$_6$): δ: 2.77(3H, d, J=4.4Hz), 6.87(2H, d, J=8.7Hz), 7.05(2H, d, J=8.8Hz), 7.38–7.42(1H, m), 7.75(1H, d, J=7.3Hz), 7.88–7.94(5H, m) FAB-MS (m/z): 503 (M + H)$^+$ |
| 39 | 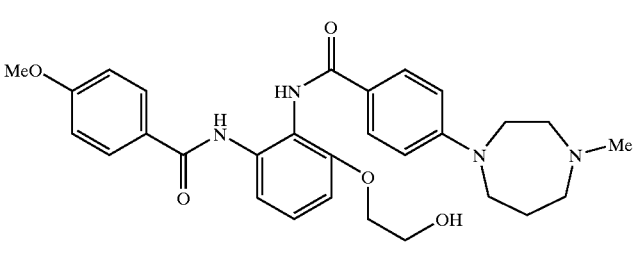 HCl | NMR(DMSO-d$_6$): δ: 2.12–2.22(1H, m), 2.26–2.39(1H, m), 2.79(3H, d, J=3.9Hz), 3.05–3.21(2H, m), 3.39–3.55(4H, m,), 3.66–3.79(3H, m), 3.81(3H, s), 3.90–3.97(1H, m), 4.11(2H, t, J=4.9Hz) 4.86(1H, br s), 6.86(2H, d, J=8.8Hz), 6.97(1H, d, J=7.4Hz), 7.04(2H, d, J=8.8Hz), 7.25–7.29(1H, m), 7.42(1H, d, J=8.3Hz), 7.86(2H, d, J=8.7Hz), 7.92(2H, d, J=8.8Hz), 9.55(1H, s), 9.89(1H, s), 10.67(1H, br s) FAB-MS (m/z): 519 (M + H)$^+$ |
| 40 | 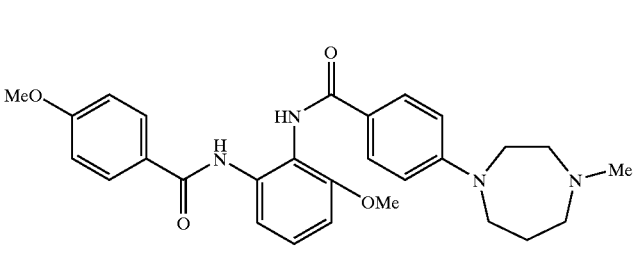 HCl | NMR(DMSO-d$_6$): δ: 2.79(3H, d, J=4.9Hz), 6.85(2H, d, J=8.8Hz), 6.95(1H, d, J=8.3Hz), 7.02(2H, d, J=8.7Hz), 7.29(1H, t, J=8.3Hz), 7.42(1H, d, J=8.3Hz), 7.84(2H, d, J=8.8Hz), 7.92(2H, d, J=8.8Hz) FAB-MS (m/z): 489 (M + H)$^+$ |

TABLE 3-continued

| Ex | structure (salt) | DATA |
|---|---|---|
| 41 | (free) | NMR(DMSO-d$_6$): δ: 2.08–2.23(2H, m), 2.84(3H, s), 3.10–4.05(11H, m), 6.93(2H, d, J=9.3Hz), 6.95(1H, d, 8.3Hz), 7.01–7.08(3H, m), 7.28(1H, t, J=8.3Hz), 7.7(1H, dd, J=1.4Hz, 8.3Hz), 7.83(2H, d, J=8.8Hz), 7.92(2H, d, J=9.2Hz) 9.4(1H, brs), 9.91(1H, s), 10.37(1H, s) FAB-MS (m/z): 553 (M − H)$^+$ |
| 42 | HCl | NMR(DMSO-d$_6$): δ: 2.79(3H, d=4.9Hz), 6.78(1H, d, J=7.8Hz), 6.82(2H, d, J=8.8Hz), 7 06(2H, d, J=8.8Hz), 7.13(1H, t, J=7.8Hz), 7.30(1H, d, J=7.8Hz), 7.75(2H, d, J=8.8Hz), 8.01(2H, d, J=8.8Hz), FAB-MS (m/z): 475 (M + H)$^+$ |
| 43 | HCl | NMR(DMSO-d$_6$): δ: 6.81(1H, dd, J=1.5, 8.3Hz), 6.86(2H, d, =8.8Hz), 7.03(2H, d, J=8.7Hz), 7.13(1H, t, J=8.3Hz), 7.25(1H, d, J=8.3Hz), 7.87(2H, d, J=8.8Hz), 7.93(2H, d, J=8.8Hz), FAB-MS (m/z): 461 (M + H)$^+$ |
| 44 | HCl | NMR(DMSO-d$_6$): δ: 0.35–0.43(2H, m), 0.61–0.67(2H, m), 1.08–1.15(1H, m) 6.81(1H, dd, J=1.0Hz, 8.8Hz), 6.86(2H, d, J=8.8Hz), 7.03(2H, d, J=8.3Hz), 7.11–7.16(1H, m), 7.24(1H, dd, J=1.0Hz, 7.9Hz), 7.87(2H, d, J=8.8Hz), 7.93(2H, d, J=8.8Hz), FAB-MS (m/z): 515 (M + H)$^+$ |
| 45 | HCl | NMR(DMSO-d$_6$): δ: 6.81(1H, d, J=8.3Hz), 6.84–6.93(2H, m), 7.03(2H, d, J=9.3Hz), 7.13(1H, t, J=8.3Hz), 7.25(1H, d, J=8.3Hz), 7.88(2H, d, J=8.2Hz), 7.92(2H, d, J=8.2Hz) FAB-MS (m/z): 502 (M + H)$^+$ |
| 46 | HCl | NMR(DMSO-d$_6$): δ: 6.80–6.86(3H, m), 7.03(2H, d, J=8.8Hz), 7.11–7.16(1H, m), 7.24(1H, dd, J=1.0Hz, 7.8Hz), 7.87(2H, d, J=8.8Hz), 7.93(2H, d, J=8.8Hz) FAB-MS (m/z): 515 (M + H)$^+$ |

TABLE 3-continued

| Ex | structure (salt) | DATA |
|---|---|---|
| 47 | 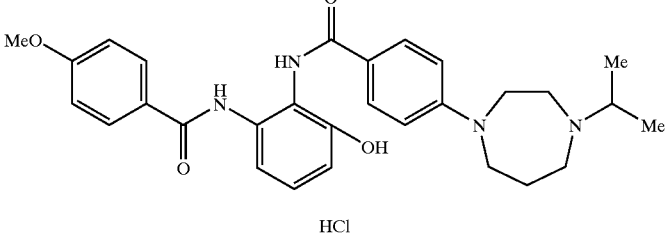 | NMR(DMSO-d$_6$): δ: 1.21–1.28(6H, m), 6.80(1H, d, J=7.9Hz), 6.85(2H, s, J=8.8Hz), 7.03(2H, d, J=8.8Hz), 7.14(1H, t, J=7.9Hz), 7.24(1H, d, J=7.8Hz), 7.86(2H, d, J=8.3Hz), 7.92(2H, d, J=8.8Hz)<br>FAB-MS (m/z): 503 (M + H)$^+$ |
| 48 | 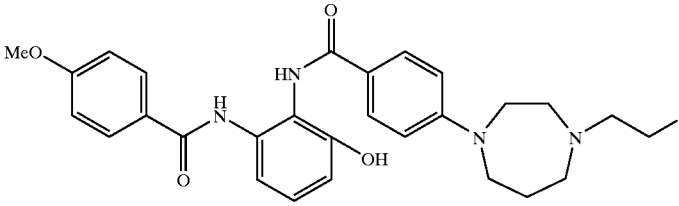 | NMR(DMSO-d$_6$): δ: 6.73–6.88(3H, m), 7.03(2H, d, J=8.8Hz), 7.14(1H, t, J=8.3Hz), 7.24(1H, dd, J=1.4Hz, 8.3Hz), 7.87(2H, d, J=8.8Hz), 7.93(2H, d, J=8.8Hz),<br>FAB-MS (m/z): 519 (M + H)$^+$ |
| 49 | 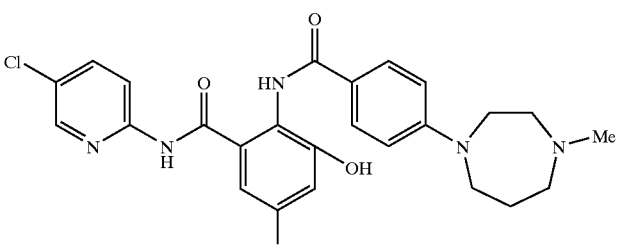 | NMR(DMSO-d$_6$): δ: 2.10–2.21(1H, m), 2.23–2.37(1H, m), 2.79(3H, d, J=4.9Hz), 3.02–3.21(2H, m), 3.37–3.56(4H, m), 3.66–3.95(2H, m), 6.81(2H, d, J=8.8Hz), 7.15(2H, s), 7.82(2H, d, J=8.8Hz), 7.89(1H, dd, J=2.5, 8.8Hz), 8.08(1H, d, J=8.8Hz), 8.36(1H, d, J=2.4Hz), 9.51(1H, s), 10.33–10.63(2H, br), 10.68(1H, s)<br>FAB-MS (m/z): 514 (M + H)$^+$ |
| 50 | 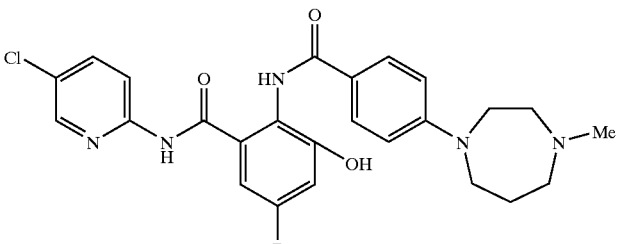 | NMR(DMSO-d$_6$): δ: 2.10–2.33(2H, m), 2.79(3H, s), 3.01–3.22(2H, m), 3.35–3.51(4H, m), 3.65–3.79(1H, m), 3.85–3.98(1H, m), 6.81(2H, d, J=8.8Hz), 7.27(2H, s), 7.82(2H, d, J=9.3Hz), 7.89(1H, dd, J=2.5, 8.8Hz), 8.08(1H, d, J=9.2Hz), 8.36(1H, d, J=2.9Hz), 9.50(1H, s), 10.37(1H, brs), 10.44(HH, s) 10.69(1H, s)<br>FAB-MS (m/z): 558, 560 (M + H)$^+$ |
| 51 | 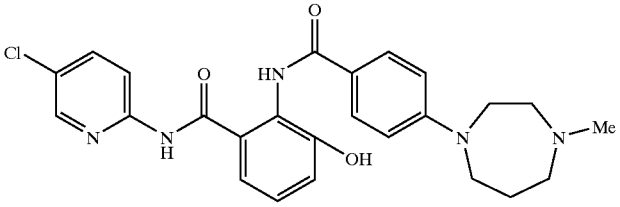 | NMR(DMSO-d$_6$): δ: 2.22(2H, brs), 2.74(3H, s), 3.00–3.60(6H, m), 3.81(2H, brs), 6.82(2H, d, J=9.3Hz), 7.10–7.25(3H, m), 7.83(2H, d, J=8.8Hz), 7.90(1H, dd, J=2.8Hz, 9.1Hz), 8.13(1H, d, J=8.7Hz), 8.35(1H, d, J=2.5Hz), 9.71(1H, s), 9.95(1H, s), 10.58(1H, s), 10.62–10.88(1H, br)<br>FAB-MS (m/z): 480 (M + H)$^+$ |

TABLE 3-continued
| Ex | structure (salt) | DATA |
|---|---|---|
| 52 | 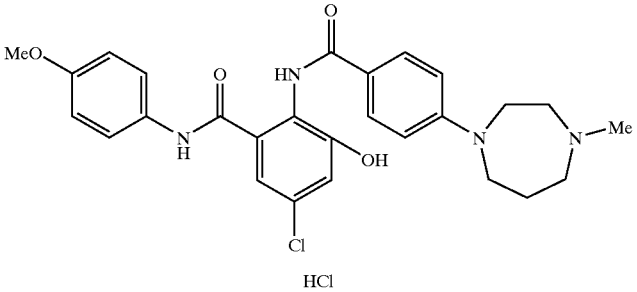 | NMR(DMSO-d$_6$): δ: 2.10–2.34(2H, m), 2.81(3H, s), 3.01–3.25(2H, m), 3.35–3.60(4H, m), 3.62–3.79(4H, m), 3.82–4.00(1H, m), 6.84(2H, d, J=9.3Hz), 6.88(2H, d, J=8.8Hz), 7.12(1H, d, J=2.5Hz), 7.18(1H, d, J=2.4Hz), 7.54(2H, d, J=9.3Hz), 7.84(2H, d, J=8.8Hz), 9.86(1H, brs), 9.96(1H, s), 10.16(1H, s), 10.43(1H, s) FAB-MS (m/z): 509 (M + H)$^+$ |
| 53 | 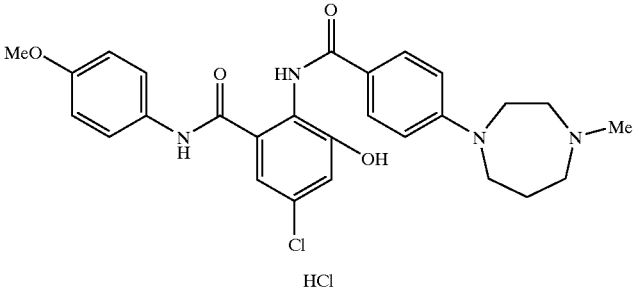 | NMR(DMSO-d$_6$): δ: 1.35(3H, t, J=7.3Hz), 2.79(3H, d, J=4.9Hz), 4.35(2H, q, J=7.3Hz), 6.85(2H, d, J=9.3Hz), 7.68–7.74(1H, m), 7.82–7.88(2H, m), 7.92–7.98(3H, m), 8.19–8.24(1H, m), 8.27(1H, s), 8.38(1H, s) FAB-MS (m/z): 559 (M + H)$^+$ |
| 54 | 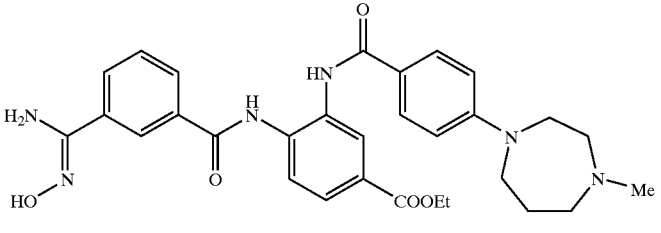 | NMR(DMSO-d$_6$): δ: 2.79(3H, d, J=4.9Hz), 6.85(2H, d, J=9.3Hz), 7.76–7.84(3H, m), 7.98(2H, d, J=8.8Hz), 8.03(1H, d, J=7.8Hz), 8.25(1H, s), 8.31(1H, d, J=7.8Hz), 8.53(1H, s), FAB-MS (m/z): 515 (M + H)$^+$ |
TABLE 4
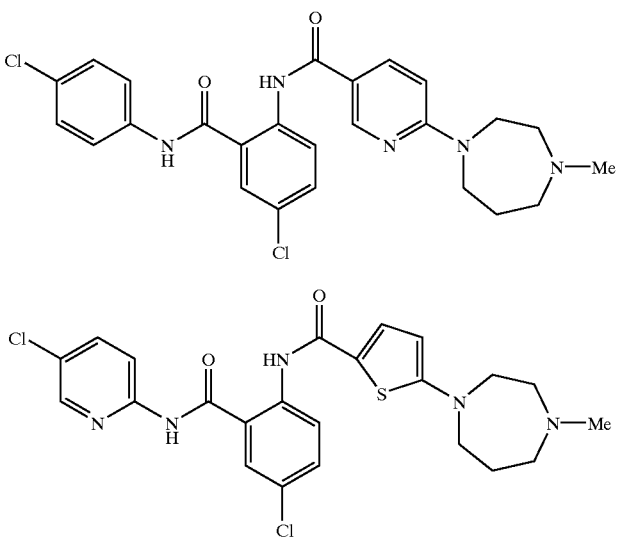

TABLE 4-continued
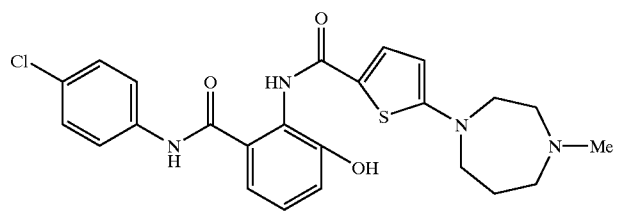
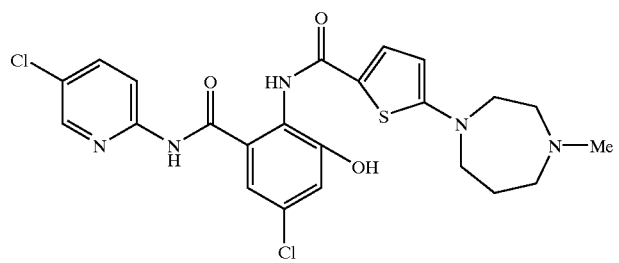
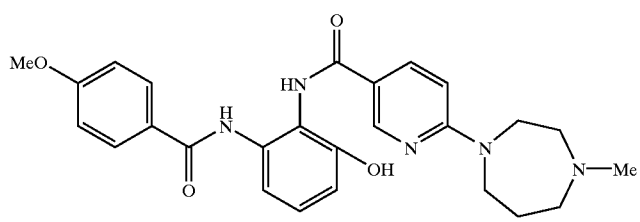
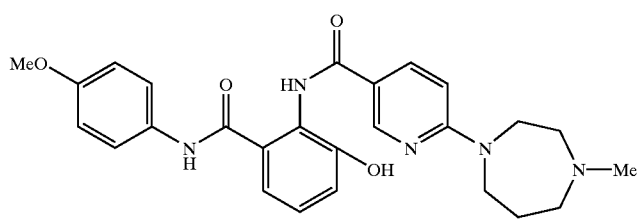
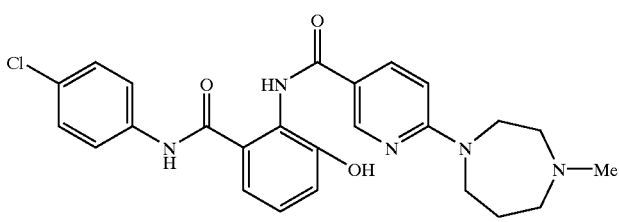
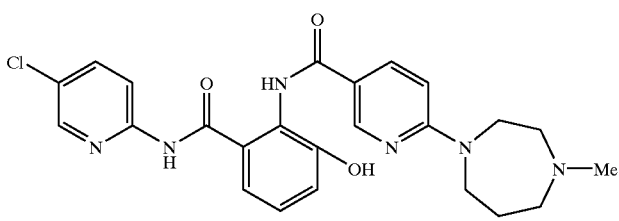
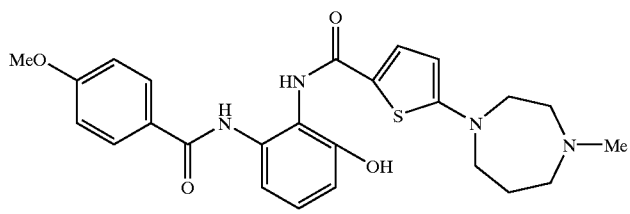

TABLE 4-continued
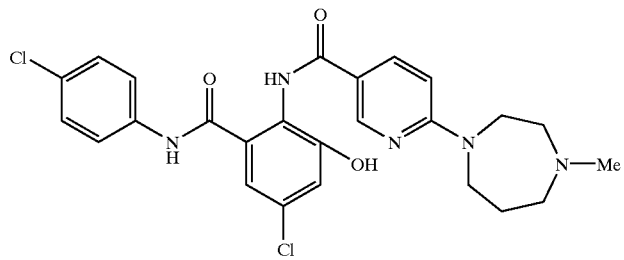
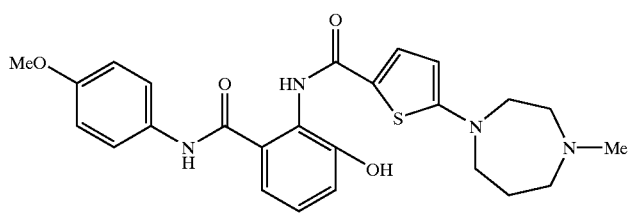
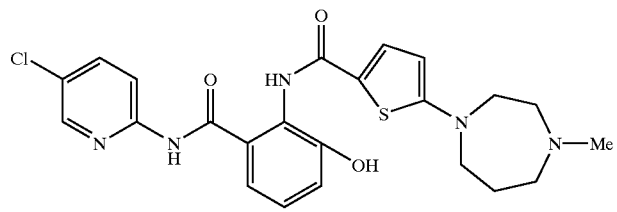
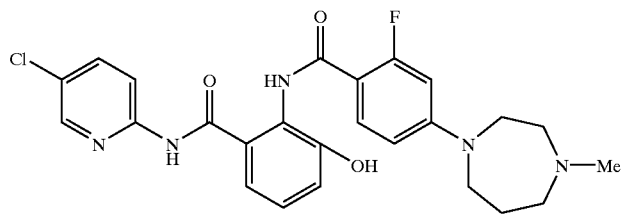
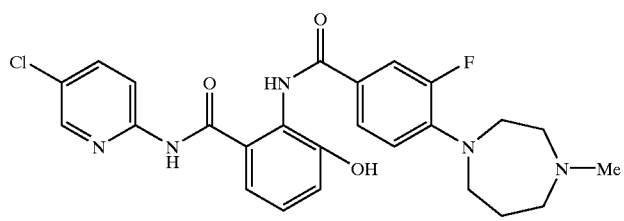
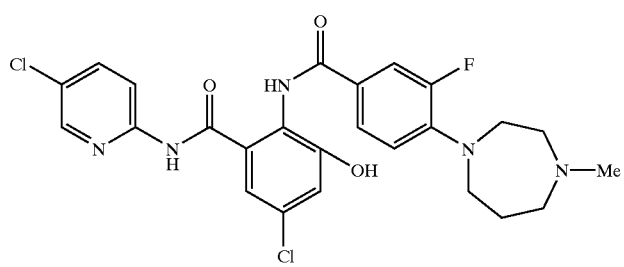

TABLE 4-continued
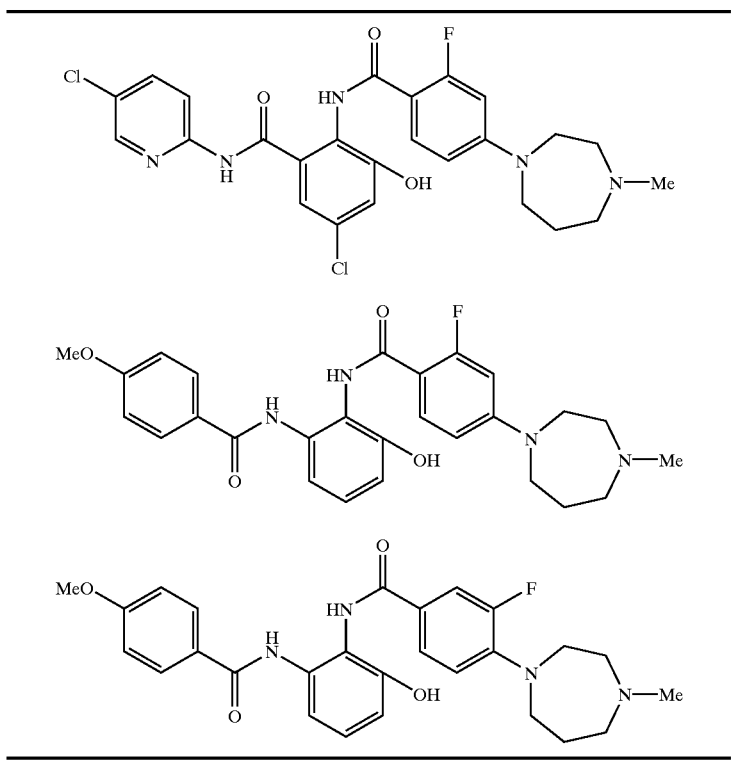
TABLE 5
![structure]
| No. | A | R² | R³ |
|---|---|---|---|
| 1 | HN=C(NH₂)-(3-methylphenyl) | OH | Cl |
| 2 |  | OH | H |
| 3 |  | H | Cl |
| 4 |  | OH | Br |
| 5 |  | H | Br |
| 6 |  | OH | F |
| 7 |  | H | F |
| 8 | HO-N=C(NH₂)-(3-methylphenyl) | OH | Cl |
TABLE 5-continued
![structure]
| No. | A | R² | R³ |
|---|---|---|---|
| 9 |  | OH | H |
| 10 |  | H | Cl |
| 11 |  | OH | Br |
| 12 |  | H | Br |
| 13 |  | OH | F |
| 14 |  | H | F |
| 15 | 4-chlorophenyl | OH | Cl |
| 16 |  | H | Cl |
| 17 |  | OH | Br |
| 18 |  | H | Br |
| 19 | 5-bromo-2-pyridyl | OH | Cl |
| 20 |  | H | Cl |
| 21 |  | OH | Br |

TABLE 5-continued

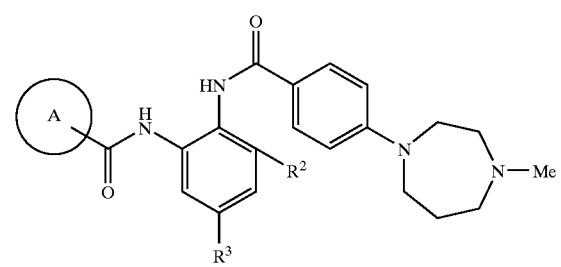

| No. | A | R² | R³ |
|---|---|---|---|
| 22 | | H | Br |
| 23 | | OH | H |
| 24 | MeO-pyridine-methyl | OH | Cl |
| 25 | | H | Cl |
| 26 | | OH | Br |
| 27 | | OH | H |
| 28 | H₂N-CH₂-(3-methylphenyl) | OH | Cl |
| 29 | | OH | H |
| 30 | | H | Cl |
| 31 | | OH | Br |
| 32 | MeO-phenyl | OH | Cl |
| 33 | | H | Cl |
| 34 | | OH | Br |
| 35 | | H | Br |
| 36 | Br-phenyl | OH | Cl |
| 37 | | H | Cl |
| 38 | | OH | Br |
| 39 | | H | Br |
| 40 | F-phenyl | OH | Cl |
| 41 | | H | Cl |
| 42 | | OH | Br |
| 43 | | H | Br |
| 44 | Cl-pyridine-methyl | OH | Cl |
| 45 | | H | Cl |
| 46 | | OH | Br |
| 47 | | H | Br |
| 48 | | OH | H |

TABLE 5-continued

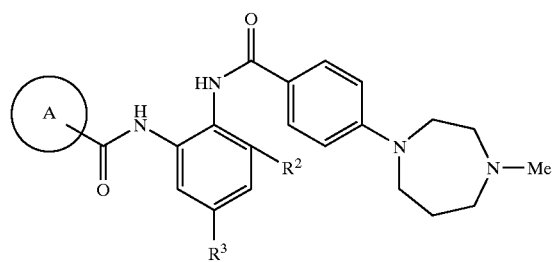

| No. | A | R² | R³ |
|---|---|---|---|
| 49 | | OH | Cl |
| | 2-methyl-1H-pyrrolo[2,3-c]pyridine | | |
| 50 | | H | Cl |
| 51 | | OH | Br |
| 52 | | H | Br |
| 53 | | OH | H |
| 54 | F-pyridine-methyl | OH | Cl |
| 55 | | H | Cl |
| 56 | | OH | Br |
| 57 | | H | Br |
| 58 | | OH | H |
| 59 | H₂N-CH₂-(4-methylphenyl) | OH | Cl |
| 60 | | OH | H |
| 61 | | H | Cl |
| 62 | | OH | Br |
| 63 | I-phenyl | OH | Cl |
| 64 | | OH | H |
| 65 | | H | Cl |
| 66 | | OH | Br |
| 67 | | H | Br |
| 68 | H₂N-C(=N-COOEt)-(3-methylphenyl) | OH | Cl |
| 69 | | OH | H |
| 70 | | H | Cl |
| 71 | | OH | Br |
| 72 | | H | Br |
| 73 | MeO-thiophene-methyl | OH | Cl |
| 74 | | OH | H |
| 75 | | H | Cl |
| 76 | | OH | Br |

TABLE 5-continued
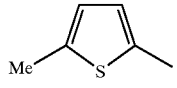
| No. | A | R² | R³ |
|---|---|---|---|
| 77 | | H | Br |
| 78 | 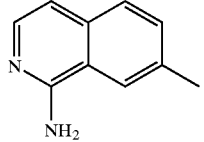 | OH | Cl |
| 79 | | H | Cl |
| 80 | | OH | Br |
| 81 | | H | Br |
| 82 | 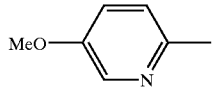 | OH | Cl |
| 83 | | OH | H |
| 84 | | H | Cl |
| 85 | | OH | Br |
| 86 | | H | Br |
| 87 | 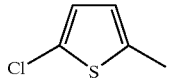 | OH | Cl |
| 88 | | OH | H |
| 89 | | H | Cl |
| 90 | | OH | Br |
| 91 | | H | Br |
| 92 | 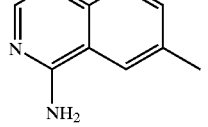 | OH | Cl |
| 93 | | OH | H |
| 94 | | H | Cl |
| 95 | | OH | Br |
| 96 | | H | Br |
| 97 | 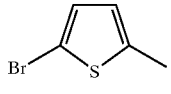 | OH | Cl |
| 98 | | OH | H |
| 99 | | H | Cl |
| 100 | | OH | Br |
| 101 | | H | Br |
| 102 | 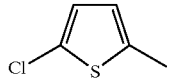 | OH | Cl |
| 103 | | OH | H |
| 104 | | H | Cl |
TABLE 5-continued
| No. | A | R² | R³ |
|---|---|---|---|
| 105 | | OH | Br |
| 106 | | H | Br |
| 107 | 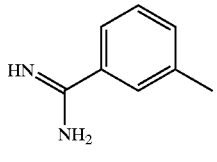 | OH | Cl |
| 108 | | OH | H |
| 109 | | H | Cl |
| 110 | | OH | Br |
| 111 | | H | Br |
| 112 | 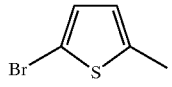 | OH | Cl |
| 113 | | H | Cl |
| 114 | | OH | Br |
| 115 | | H | Br |
| 116 | 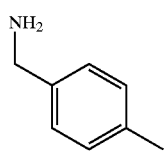 | OH | Cl |
| 117 | | H | Cl |
| 118 | | OH | Br |
| 119 | | H | Br |
| 120 | | OH | F |
| 121 |  | OH | Cl |
| 122 | | OH | H |
| 123 | | H | Cl |
| 124 | | OH | Br |
| 125 | | H | Br |
| 126 | | OH | F |
| 127 | | H | F |
| 128 |  | OH | Cl |
| 129 | | OH | H |
| 130 | | H | Cl |
| 131 | | OH | Br |
| 132 | | H | Br |

TABLE 5-continued

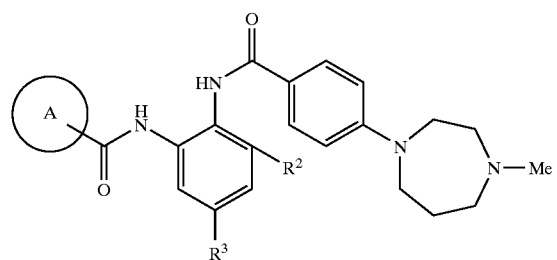

| No. | A | R² | R³ |
|---|---|---|---|
| 133 | Cl-C6H4- | OH | Cl |
| 134 | | H | Cl |
| 135 | | OH | Br |
| 136 | | H | Br |
| 137 | Br-pyridyl-Me | OH | Cl |
| 138 | | H | Cl |
| 139 | | OH | Br |
| 140 | | H | Br |
| 141 | | OH | H |
| 142 | MeO-pyridyl-Me | OH | Cl |
| 143 | | H | Cl |
| 144 | | OH | Br |
| 145 | | H | Br |
| 146 | | OH | H |
| 147 | NH2-CH2-C6H4-(4-Me) | OH | Cl |
| 148 | | OH | H |
| 149 | | OH | Br |
| 150 | | H | Cl |
| 151 | MeO-C6H4- | H | Cl |
| 152 | | OH | Br |
| 153 | | H | Br |
| 154 | | OH | F |
| 155 | Br-C6H4- | OH | Cl |
| 156 | | H | Cl |
| 157 | | OH | Br |
| 158 | | H | Br |
| 159 | F-C6H4- | OH | Cl |

TABLE 5-continued

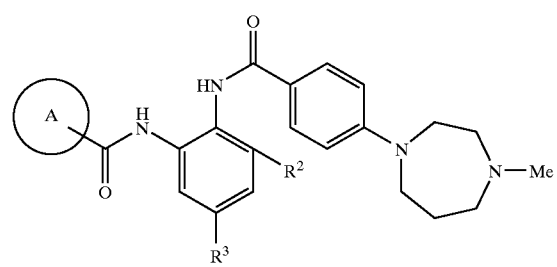

| No. | A | R² | R³ |
|---|---|---|---|
| 160 | | H | Cl |
| 161 | | OH | Br |
| 162 | | H | Br |
| 163 | Cl-pyridyl-Me | H | Br |
| 164 | | OH | F |
| 165 | H2N-CH2-C6H4- (3-Me) | OH | Cl |
| 166 | | H | Cl |
| 167 | | OH | Br |
| 168 | | H | Br |
| 169 | | OH | H |
| 170 | F-pyridyl-Me | OH | Cl |
| 171 | | H | Cl |
| 172 | | OH | Br |
| 173 | | H | Br |
| 174 | | OH | H |
| 175 | | OH | F |
| 176 | F-pyridyl-Me | OH | Cl |
| 177 | | H | Cl |
| 178 | | OH | Br |
| 179 | | H | Br |
| 180 | | OH | H |
| 181 | I-C6H4- | OH | Cl |
| 182 | | OH | H |
| 183 | | H | Cl |
| 184 | | OH | Br |
| 185 | | H | Br |
| 186 | H2N-C(=N-COOEt)-C6H4-(3-Me) | OH | Cl |

TABLE 5-continued

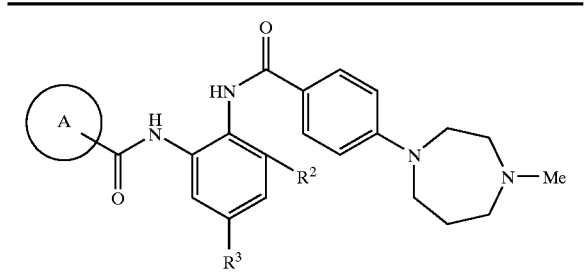

| No. | A | R² | R³ |
|---|---|---|---|
| 187 | | OH | H |
| 188 | | H | Cl |
| 189 | | OH | Br |
| 190 | | H | Br |
| 191 | 6-methyl-1H-indol-yl | OH | Cl |
| 192 | | OH | H |
| 193 | | H | Cl |
| 194 | | OH | Br |
| 195 | | H | Br |
| 196 | 2,5-dimethylthiophene | OH | Cl |
| 197 | | OH | H |
| 198 | | H | Cl |
| 199 | | OH | Br |
| 200 | | H | Br |
| 201 | 5-MeO-2-methylpyridine | OH | Cl |
| 202 | | OH | H |
| 203 | | H | Cl |
| 204 | | OH | Br |
| 205 | | H | Br |
| 206 | 1-amino-7-methylisoquinoline | OH | Cl |
| 207 | | OH | H |
| 208 | | H | Cl |
| 209 | | OH | Br |
| 210 | | H | Br |
| 211 | 2-Cl-5-methylthiophene | OH | Cl |
| 212 | | OH | H |
| 213 | | H | Cl |
| 214 | | OH | Br |
| 215 | | H | Br |

TABLE 5-continued

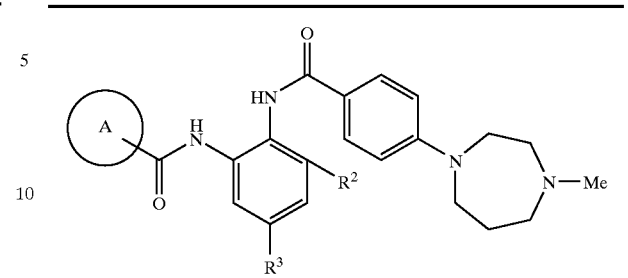

| No. | A | R² | R³ |
|---|---|---|---|
| 216 | 2-Br-5-methylthiophene | OH | Cl |
| 217 | | OH | H |
| 218 | | H | Cl |
| 219 | | OH | Br |
| 220 | | H | Br |
| 221 | 4-amino-6-methylquinazoline | OH | Cl |
| 222 | | OH | H |
| 223 | | H | Cl |
| 224 | | OH | Br |
| 225 | | H | Br |
| 226 | 1-amino-7-methylisoquinoline | OH | Cl |
| 227 | | OH | H |
| 228 | | H | Cl |
| 229 | | OH | Br |
| 230 | | H | Br |
| 231 | 2-Cl-5-methylthiophene | OH | Cl |
| 232 | | H | Cl |
| 233 | | OH | Br |
| 234 | | H | Br |
| 235 | | OH | H |
| 236 | 2-Br-5-methylthiophene | OH | Cl |
| 237 | | H | Cl |
| 238 | | OH | Br |
| 239 | | H | Br |
| 240 | | OH | H |

TABLE 6

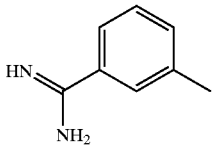

| No. | A | X¹ | R³ |
|---|---|---|---|
| 1 | 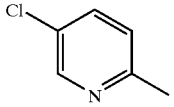 | —CH₂—CH₂— | H |
| 2 |  | —CH₂—CH₂— | Cl |
| 3 |  | —NH—CH₂— | H |
| 4 |  | —NH—CH₂— | Cl |
| 5 |  | —O—CH₂— | H |
| 6 |  | —O—CH₂— | Cl |
| 7 |  | (E) —CH=CH— | H |
| 8 |  | (E) —CH=CH— | Cl |
| 9 | 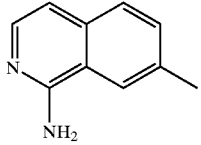 | —CH₂—CH₂— | H |
| 10 |  | —CH₂—CH₂— | Cl |
| 11 |  | —NH—CH₂— | H |
| 12 |  | —NH—CH₂— | Cl |
| 13 |  | —O—CH₂— | H |
| 14 |  | —O—CH₂— | Cl |
| 15 |  | (E) —CH=CH— | Cl |
| 16 | 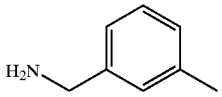 | —CH₂—CH₂— | H |
| 17 |  | —CH₂—CH₂— | Cl |
| 18 |  | —NH—CH₂— | H |
| 19 |  | —NH—CH₂— | Cl |
| 20 |  | —O—CH₂— | H |
| 21 |  | —O—CH₂— | Cl |
| 22 |  | (E) —CH=CH— | H |
| 23 |  | (E) —CH=CH— | Cl |
| 24 | 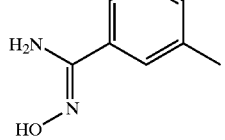 | —CH₂—CH₂— | H |
| 25 |  | —CH₂—CH₂— | Cl |
| 26 |  | —NH—CH₂— | H |
| 27 |  | —NH—CH₂— | Cl |
| 28 |  | —O—CH₂— | H |
| 29 |  | —O—CH₂— | Cl |
| 30 |  | (E) —CH=CH— | H |
| 31 |  | (E) —CH=CH— | Cl |
| 32 | 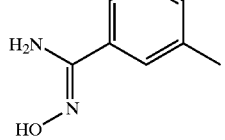 | —CH₂—CH₂— | H |
| 33 |  | —CH₂—CH₂— | Cl |
| 34 |  | —NH—CH₂— | H |
| 35 |  | —NH—CH₂— | Cl |
| 36 |  | —O—CH₂— | H |
| 37 |  | —O—CH₂— | Cl |
| 38 |  | (E) —CH=CH— | H |
| 39 |  | (E) —CH=CH— | Cl |
| 40 | 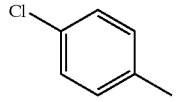 | —CH₂—CH₂— | H |
| 41 |  | —CH₂—CH₂— | Cl |
| 42 |  | —NH—CH₂— | H |
| 43 |  | —NH—CH₂— | Cl |
| 44 |  | —O—CH₂— | H |
| 45 |  | —O—CH₂— | Cl |
| 46 |  | (E) —CH=CH— | Cl |
| 47 | 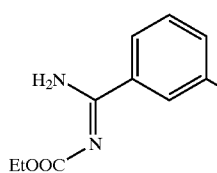 | —CH₂—CH₂— | H |
| 48 |  | —CH₂—CH₂— | Cl |
| 49 |  | —NH—CH₂— | H |
| 50 |  | —NH—CH₂— | Cl |
| 51 |  | —O—CH₂— | H |
| 52 |  | —O—CH₂— | Cl |
| 53 |  | (E) —CH=CH— | H |
| 54 |  | (E) —CH=CH— | Cl |
| 55 | 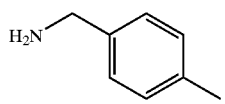 | —CH₂—CH₂— | H |
| 56 |  | —CH₂—CH₂— | Cl |
| 57 |  | —NH—CH₂— | H |
| 58 |  | —NH—CH₂— | Cl |
| 59 |  | —O—CH₂— | H |
| 60 |  | —O—CH₂— | Cl |
| 61 |  | (E) —CH=CH— | H |
| 62 |  | (E) —CH=CH— | Cl |

What is claimed is:

1. A diazepan compound represented by the following formula (I) or a salt thereof;

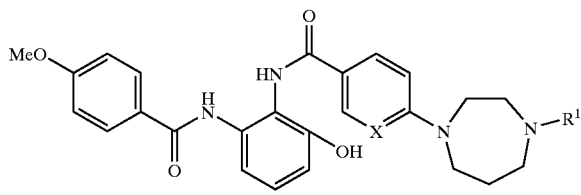

(I)

wherein

R¹ is lower alkyl; and

X is N, or CH.

2. A 3-hydroxy-N¹-(4-methoxybenzoyl)-N²-[4-(4-methyl-1,4-diazepan-1-yl)benzoyl]-1,2-phenylenediamine or a salt thereof.

3. A 3-hydroxy-N¹-(4-methoxybenzoyl)-N²-[6-(4-methyl-1,4-diazepan-1-yl)nicotinoyl]-1,2-phenylenediamine or a salt thereof.

4. A 3-hydroxy-N²-[4-(4-isopropyl-1,4-diazepan-1-yl)benzoyl]-N¹-(4-methoxybenzoyl)-1,2-phenylenediamine or a salt thereof.

5. A pharmaceutical composition containing the diazepan compound or a salt thereof according to claim 1 as an effective ingredient and a pharmaceutically acceptable carrier.

6. An activated blood coagulation factor X inhibitor in which the diazepan compound or a salt thereof according to claim 1 is an effective ingredient.

* * * * *